(12) United States Patent
Ciaccio et al.

(10) Patent No.: US 6,847,839 B2
(45) Date of Patent: Jan. 25, 2005

(54) SYSTEM AND METHOD FOR DETERMINING REENTRANT VENTRICULAR TACHYCARDIA ISTHMUS LOCATION AND SHAPE FOR CATHETER ABLATION

(75) Inventors: Edward J. Ciaccio, Cherry Hill, NJ (US); Andrew L. Wit, Massapequa, NY (US); Alexis Christine Tosti, Gladstone, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/918,216

(22) Filed: Jul. 30, 2001

(65) Prior Publication Data

US 2003/0023130 A1 Jan. 30, 2003

(51) Int. Cl.⁷ .................................................. A61B 5/04
(52) U.S. Cl. ...................................................... 600/512
(58) Field of Search ................................ 600/509, 515, 600/516–518

(56) References Cited

U.S. PATENT DOCUMENTS 6,236,883 B1   5/2001   Ciaccio et al.

OTHER PUBLICATIONS

Spach, MS, et al. "The functional role of structural complexities in the propagation of depolarization in the atrium of the dog", Circulation Research, (1982) 50:175–191.

Gardner, PI, et al. "Electrophysiologic and anatomic basis for fractioned electrograms recorded from healed myocardial infarcts", Circulation, (1985) 72:596–611.

Pogwizd, S.M., and Corr P.B., "Reentrant and nonreentrant mechanisms contribute to arrhythmogenesis during early myocardial ischemia: results using three–dimensioanl mapping" Circualtion Research, (1987) 61:352–371.

Dillon, S.M., et al. "Influences of anisotropic tissue structure on reentrant circuits in the epicardial border zone of subacute canine infarcts", Circulation Research, (1988) 63:182–206.

Chinushi, M., et al. "Proarrhythmic effects of antiarrhythmic drugs assessed by electrophysiologic study in recurrent sustained ventricular tachycardia", Jpn Circ J, (1991) 55:133–141.

Smith, J.H., et al. "Altered patterns of gap junctional distribution in ischemic heart disease: an immunohistochemical study of human myocarium using laser scanning confocal microscopy", Am J Path, (1991) 139:801–821.

(List continued on next page.)

Primary Examiner—Mark Bockelman
(74) Attorney, Agent, or Firm—John P. White; Cooper & Dunham LLP

(57) ABSTRACT

A method for identifying and localizing a reentrant circuit isthmus in a heart of a subject during sinus rhythm, including: a) receiving electrogram signals from the heart during sinus rhythm via electrodes; b) storing the electrogram signals; c) creating a map based on the electrogram signals; d) finding a center reference activation location on the map; e) defining measurement vectors originating from the center reference activation location; f) selecting from the measurement vectors a primary axis vector indicating a location of the reentrant circuit isthmus in the heart; g) finding threshold points of electrogram signals on the map; h) connecting the threshold points to form a polygon indicating a shape of the reentrant circuit isthmus in the heart.

33 Claims, 13 Drawing Sheets

OTHER PUBLICATIONS

Rohr, S., and Salzberg, B.M., Characterization of impulse propagation at the microscopic level across geometrically defined expansions of excitable tissue: multiple site optical recording transmembrane voltage (MSORTV) in patterned growth heart cell cultures, J Gen Physiol,, (1994) 104:287–309.

Miller, J.M., et al., "Effect of Subendocardial Resection on Sinus Rhythm Endocardial Electrogram Abnormalities", Circulation, (1995) 91:2385–2391.

Stevenson, W.G., et al., "Relation of pace–mapping QRS configuration and conduction delay to ventricular tachycardia reentry circuitsin human infarct scars", J Am Coll Cardiol., (1995) 26: 481–488.

Bogun, F., et al., "Comparison of effective and ineffective target sites that demonstrate concealed entrainment in patients with coronary artery disease undergoing radiofreqeuency ablation of ventricular tachycardia", Circulation, (1997) 95: 183–190.

Hadjis, T.A., et al., "Effect of recording site of postpacing interval measurement during catheter mapping and entrainment of posinfarction ventricular tachycardia", J Cardiovasc Electorphysiol., (1997) 8:398–404.

Harada, T., et al., "Catheter ablation of ventricular tachycardia after myocardial infarction: relationship of endocardial sinus rhythm late potentials to the reentry circuit", JACC, (1997) 30:1015–1023.

Josephson, M.E., et al., "Pathophysiologic substrate for sustained ventricular tachycardia after myocardial infarction: relationship of endocardial sinus rhythm late potentials to the renetry circuit", JACC, (1997) 30:1015–1023.

Peters, N.S., et al., "Disturbed connexin43 gap junction distribution correlates with the location of reenetrant circuits in the epicardial border zone of healing canine infarcts that cause ventricular tachycardia", Circulation, (1997) 95:988–996.

Peters, N.S., et al., "Characteristics of the temporal and spatial excitable gap in anisotropic reentrant circuits causing sustained ventricular tachycardia", Circ Res, (1998) 82:279–293.

Pogwizd, S.M., et al., "Mechanisms underlying spontaneous and induced ventricular arrhythmias in patients with idiopathic dilated cardiomyopathy", Circulation, (1998) 98:2404–2414.

Schilling, R.J., et al., "Simultaneous endocardial mapping in the human left ventricle using a non–contact catheter", Circulation, (1998) 98:887–898.

Stevenson, W.G., et al., "Radiofrequency catheter ablation of ventricular tachycardia after myocardial infarction", Circulation, (1998) 98:308–314.

Bogun, F., et al., "Clinical value of the postpacing interval for mapping of ventricular tachycardia in patients with prior myocardial infarction", J Cardiovas Electrophysiol., (1999) 10: 43–51.

Schilling, R.J., et al., "Feasibility of a non–contact catheter for endocardial mapping of human ventricular Tachydcardia", Circulation, (1999) 99:2543–2552.

Ciaccio, E.J., et al., "Dynamic Changes in Electogram Morphology at Functional Lines of Block in Reentrant Circuits During Ventricular Tachycardia in the Infarcted Canine Heart: A New Method to Localize Reentrant Circuits from electrogram Features Using Adaptive Template Matching", J Cardiovasc Electrophysiol., (199) vol. 10, pp. 194–213.

Ciaccio, E.J., "Localization of the slow conduction zone during reentrant ventricular tachycardia", Circulation, (2000) 102: 464–469.

Ciaccio, E.J., et al., "Relationship of Specific Electrogram Characteristics During Sinus Rhythm and Ventricular Pacing Determined by Adaptive Template matching to the Location of Functional Reentrant Circuits that Cause Ventricular Tachycardia in the Infarcted Canine Heart", J Cardiovasc Electrophysiol,, (2000) vol. 11, pp. 446–457.

Ellison, K.E., et al., "Catheter ablation for hemodynamically unstable monomorphic ventricular Tachycardia", JCE, (2000) 11:41–44.

Ciaccio, E.J., et al., "Relationship between Sinus Rhythm Activation and the Reentrant Ventricular Tachycardia Isthmus", Circulation, (2001) 104:613–619.

Ciaccio, E.J., "Dynamic relationship of cycle length to reentrant circuit geometry and to the slow conduction zone during ventricular tachycardia", Circulation, (2001) 103:1017–1024.

Ciaccio, E.J., et al. "Static Relationship of Cycle Length to Reentrant Circuit Geometry", Circulation, (2001) 104:1946–1951.

Soejima, K, et al., "Catheter ablation in patients with multiple and unstable ventricular tachycardias after myocardial infarction: short ablation lines guided by reentry circuit isthumuses and sinus rhythm mapping", Circulation, (2001) 104:664–9.

Ciaccio, E.J., "Premature excitation and onset of reentrant tachycardia", Am J Physiol Heart Circ Physoil, (2002) vol. 283:H1–H11.

Scherlag, BJ, et al. "Sustained ventricular tachycardia: common functional properties of different anatomical Substrates", In Zipes DP, Jalife J. eds. Cardiac electrophysiology and arrhythmias. Orlando Fla: Grune and Stratton, (1985) 379–387.

Kogan, B.Y., et al. "Excitation wave propagation within narrow pathways: Geometric configurations facilitating unidirectional block and reentry", Physica D, (1992) 59:275–296.

Stevenson, W.G., et al. "Identification of reentry circuit sites during catheter mapping and radiofrequency ablation of ventricular tachycardia late after myocardial infarction", Circulation, (1993) 88:1647–1670.

Wit, A.L., and Janse, M.J., "Basic mechanisms of arrhythmias", In: Wit AL and Janse MJ, eds. The ventricular arrhythmias of ischemia and infarction, New York, NY: Futura, (1993) 1–160.

Blanchard, S.M., et al., "Why is catheter ablation less successful than surgery for treating ventricular tachycardia that results from coronary artery disease?", PACE, (1994) 17:2315–2335.

Cabo, C., et al., "Wave–front curvature as a cause of slow conduction and block in isolated cardiac Muscle", Circulation Research, (1994) 75:1014–1028.

Aizawa, Y., et al., "Catheter ablation of ventricular tachycardia with radiofrequency currents, with special reference to the termination and minor morphologic change of reinduced ventricular tachycardia", AM J Cardiol., (1995) 76:574–579.

Downar, E., et al., "Endocardial mapping of ventricular tachycardia in the intact human ventricle. III. Evidence of multiuse reentry with spontaneous and induced block in portions of the reentrant path complex", JACC, (1995) 25:1591–1600.

El–Sherif, N., "The figure–8 model of reentrant excitation in the canine postinfarction Heart", In Zipes DP, Jalife J, eds: Cardiac Electrophysiology: From Cell to Bedside, WB, Saunders, Philadelphia, (1995) 363–378.

Russ, J.C., "The Image Processing Handbook", Boca Raton, FLa:CRC Press, (1995) 456–462.

Sato, M., et al., "The efficacy of radiofrequency catheter ablation for the treatment of ventricular tachycardia associated with cardiomyopathy", Jpn Cic J., (1997) 61:55–63.

Ellison, K.E., et al., "Entrainment mapping and radiofrequency catheter ablation of ventricular tachycardia in right ventricular dysplasia", J Am Coll Cardiol., (1998) 32: 724–728.

Krishnan, S.C., and Josephson, M.E., "Mapping techniques and catheter ablation of ventricular tachycardia due to coronary artery disease", Arch Mal Coeur Vaiss., (1998) 91: 21–26.

Rohr, S., et al., "Optical recording of impulse propagation in designer cultures. Cardiac tissue architectures inducing ultra–slow conduction", Trends in Cardiovascular Medicine, (1999) 9:173–179.

Schilling, R.J., et al., "Characteristic of sinus rhythm electorgrams at sites of ablation of ventricular tachycardia relative to all other sites: a non–contact mapping study of the entire left ventricle", JCE, (1998) 9:921–933.

Fig. 3A
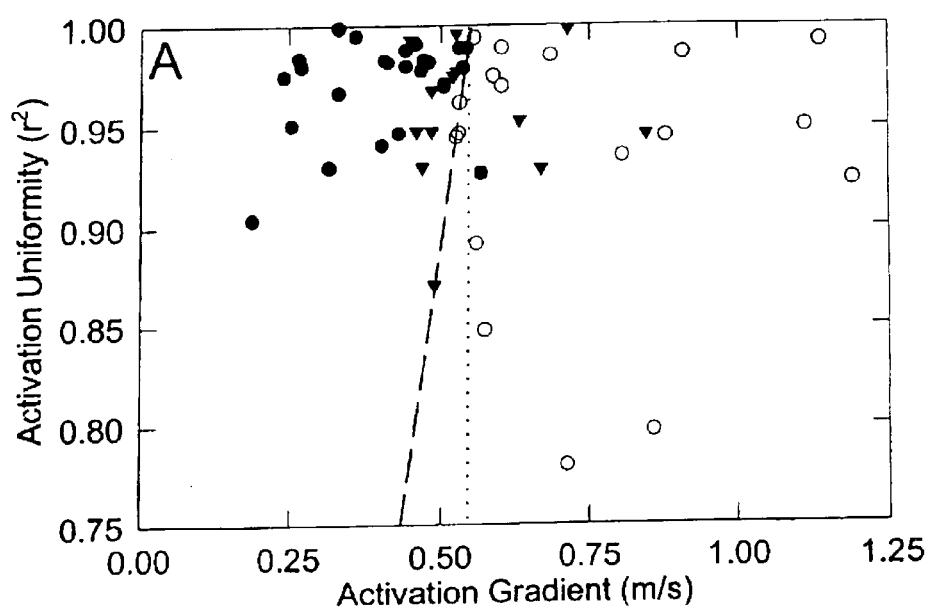
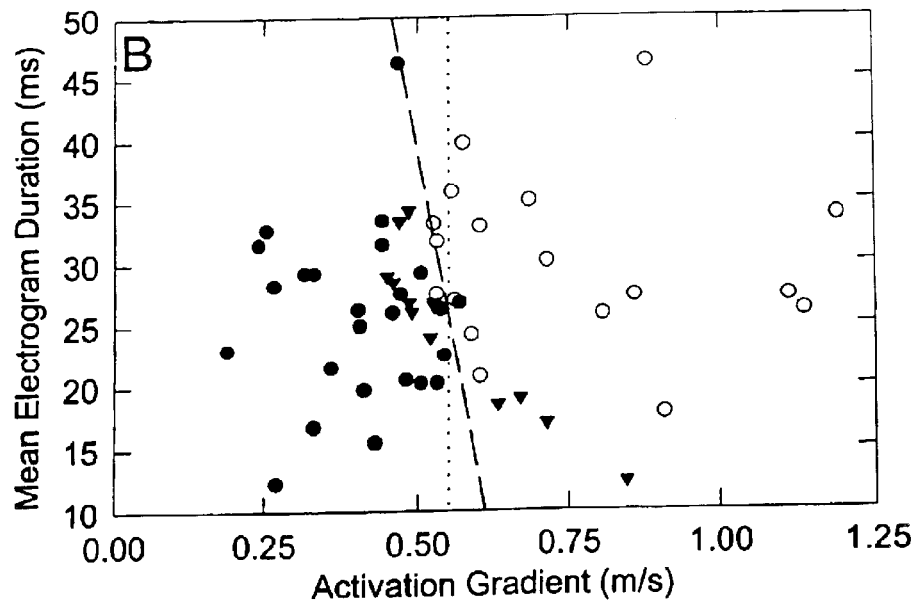
Fig. 3B

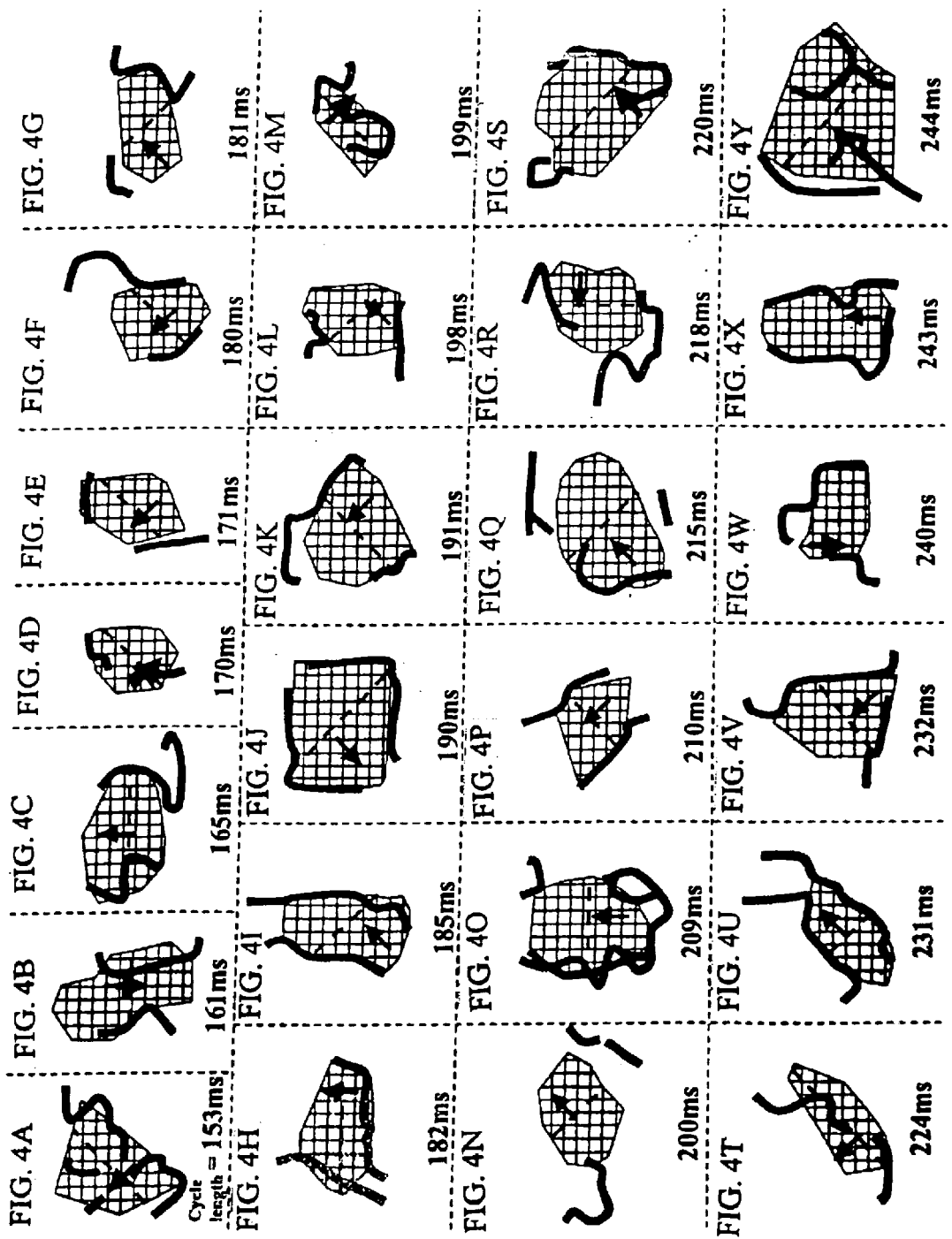

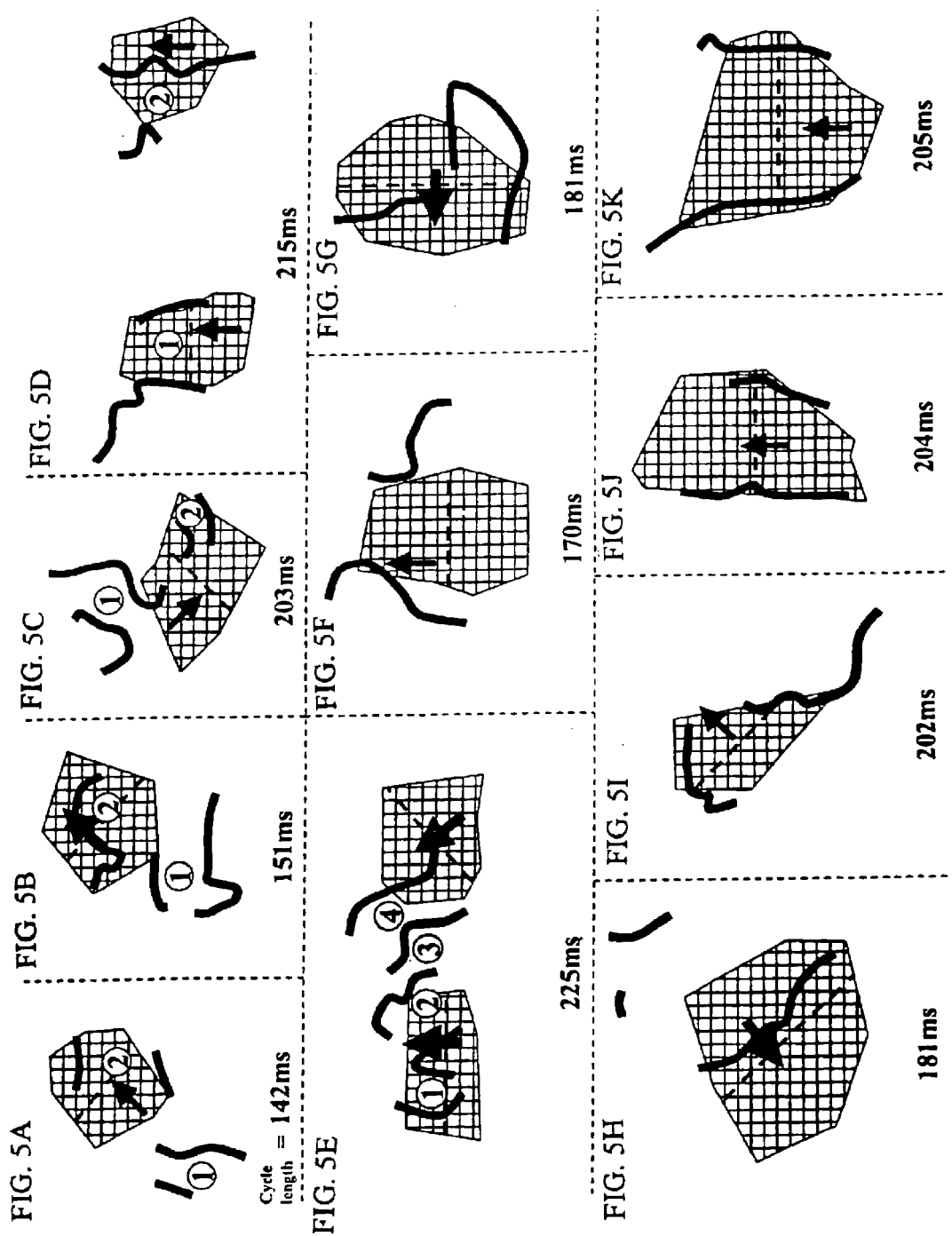

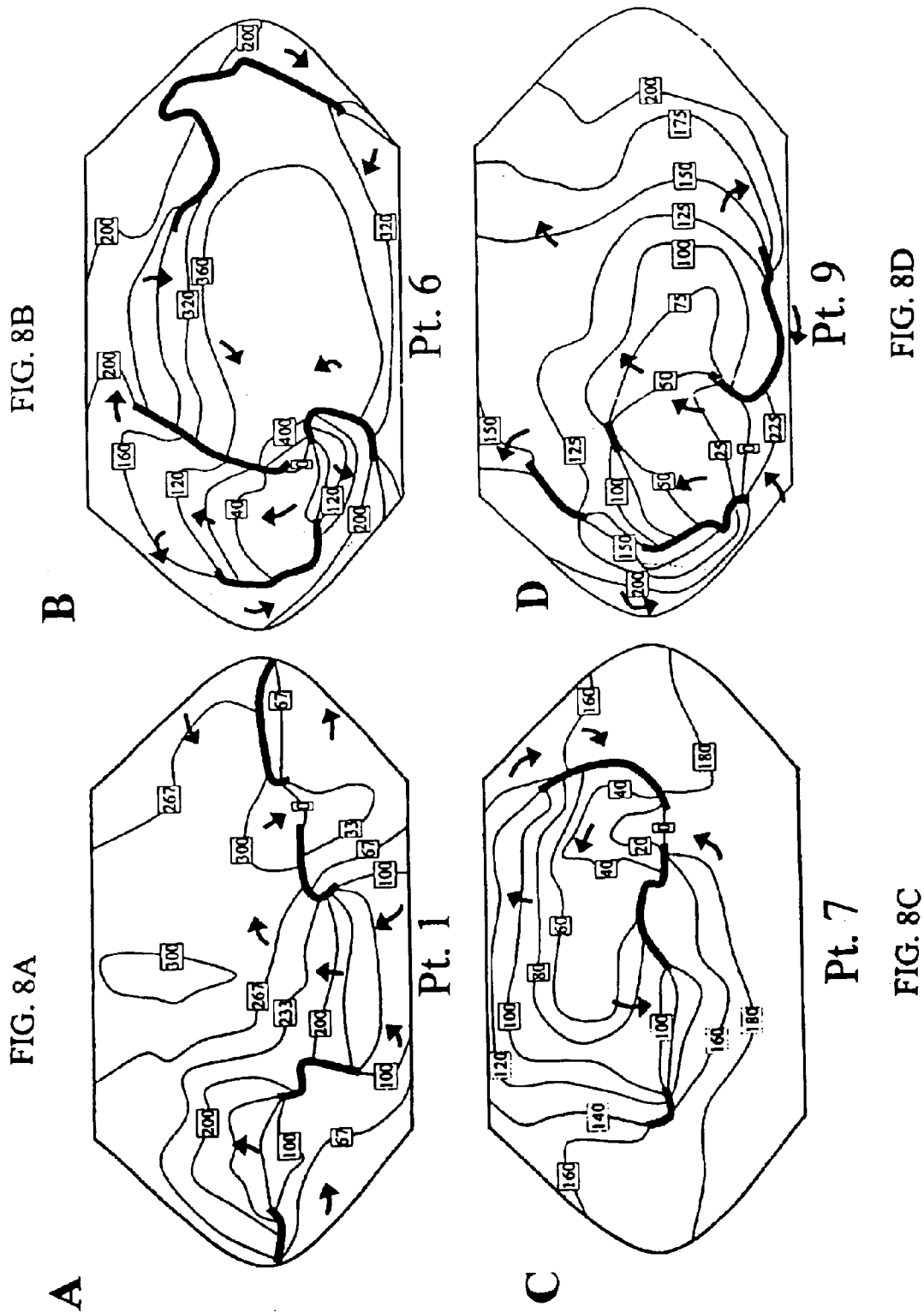

Pt. 5

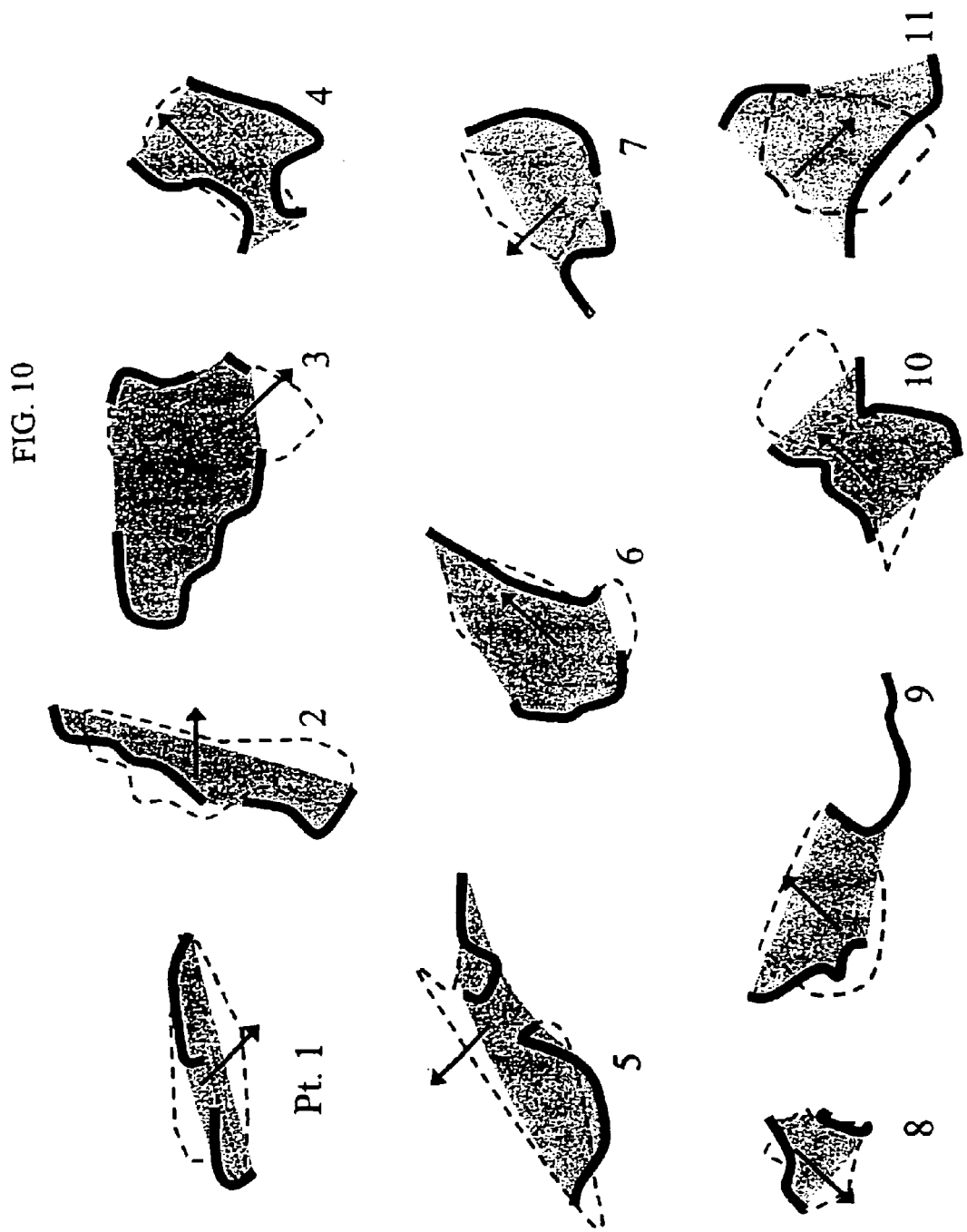

FIG. 12

Patient Clinical Data

| Patient | Sex | Infarct Location | Time from MI to EP Study (years) | Drug Therapy | VT Cycle-Length at Onset (ms) |
|---|---|---|---|---|---|
| 1 | M | Ant | 3 | Amiodarone | 328 |
| 2 | M | Inf-lat | 11 | Sotolol | 368 |
| 3 | M | Multiple | 9 | Amiodarone | 432 |
| 4 | M | Ant | 15 | Amiodarone | 272 |
| 5 | M | Post | 5 | Amiodarone | 251 |
| 6 | M | Multiple | 12 | Amiodarone + mex | 473 |
| 7 | M | Inf-lat | 5 | Amiodarone + mex | 197 |
| 8 | M | Inf | 2 | Amiodarone | 401 |
| 9 | M | Inf-lat | 4 | Amiodarone | 243 |
| 10 | F | Inf | 1 | Amiodarone | 287 |
| 11 | M | Inf | 2 | Amiodarone | 252 (no reentry) |
| 12 | M | Ant | 14 | Sotolol | 384 |
| 13 | M | Ant | 1 | Amiodarone | 249 (no reentry) |
| 14 | M | Ant | 11 | Amiodarone | 223 (no reentry) |

SYSTEM AND METHOD FOR DETERMINING REENTRANT VENTRICULAR TACHYCARDIA ISTHMUS LOCATION AND SHAPE FOR CATHETER ABLATION

The invention of the present disclosure was made from Government support under Grant HL-31393 and Project Grant HL-30557 from the Heart, Lung and Blood Institutes, National Institutes of Health, a Research Grant from the Whitaker Foundation, and the American Heart Association Established Investigator Award. Accordingly, the U.S. Government has certain rights to this invention.

Throughout this disclosure, various publications may be referenced by Arabic numerals in brackets. Disclosures of these publications in their entireties are hereby incorporated by reference into this application to more fully describe the state of the art to which this disclosure pertains. Full citations of these publications may be found at the end of the specification.

BACKGROUND OF THE INVENTION

In canine hearts with inducible reentry, the isthmus tends to form along an axis from the area of last to first activity during sinus rhythm. It was hypothesized that this phenomenon could be quantified to predict reentry and the isthmus location. An in situ canine model of reentrant ventricular tachycardia occurring in the epicardial border zone was used in 54 experiments (25 canine hearts in which primarily long monomorphic runs of figure-8 reentry was inducible, 11 with short monomorphic or polymorphic runs, and 18 lacking inducible reentry). From the sinus rhythm activation map for each experiment, the linear regression coefficient and slope was calculated for the activation times along each of 8 rays extending from the area of last-activation. The slope of the regression line for the ray with greatest regression coefficient (called the primary axis) was used to predict whether or not reentry would be inducible (correct prediction in 48/54 experiments). For all 36 experiments with reentry, isthmus location and shape were then estimated based on site-to-site differences in sinus rhythm electrogram duration. For long and short-runs of reentry, estimated isthmus location and shape partially overlapped the actual isthmus (mean overlap of 71.3% and 43.6%, respectively). On average for all reentry experiments, a linear ablation lesion positioned across the estimated isthmus would have spanned 78.2% of the actual isthmus width. Parameters of sinus rhythm activation provide key information for prediction of reentry inducibility, and isthmus location and shape.

During ventricular tachycardia, the heart beats rapidly which can be debilitating to the patient and cause such things as tiredness and even syncope (i.e. fainting). This clinical problem usually follows a myocardial infarction (heart attack) and is caused by abnormal electrical conduction in the heart because the cells become damaged during the infarct. When conduction is slow and abnormal, a process called reentry can occur in which the propagating electrical wavefront travels in a circle, or double loop, and reenters the area where it had previously traveled. This propagation around the loop(s) occurs very rapidly, and a heartbeat occurs once each time the propagating wavefront traverses around the loop or loops. Since the condition is abnormal, the heart muscle does not contract as it should, so that the strength of the pumping action is reduced, and the rapidity of the heartbeat causes the heart chambers to not fill with blood completely. Therefore, because of both the poor filling action and the poor pumping action, there is less blood delivered to the tissues. This causes the maladies that the patient experiences.

A promising cure for this ailment is radio-frequency catheter ablation, which does not require surgery and is permanent. In the ablation procedure, a catheter is inserted through an artery of the patient and is positioned in the heart chamber. At the appropriate location on the inner heart surface, known as the endocardium, radio-frequency energy is delivered from the tip of the catheter to the heart tissue, thereby blocking conduction at the place of delivery of the energy, which is called the target site on the heart. Ideally, energy is delivered to the location between the double loop where the electrical wavefront propagates. This is called the best, or optimal target site. However, it is sometimes difficult to locate the best target site, and also the precise surface area to which energy should be delivered is often unknown and presently must be done by trial and error.

The present disclosure describes a system and method for determining the shape and location of the target site, which is called the reentry isthmus. U.S. Pat. No. 6,236,883 to Ciaccio et al describes a method to find the isthmus based on signals acquired while the heart was undergoing ventricular tachycardia.

Although this former method potentially represents a substantial improvement over existing methods, it is not always convenient and cannot be used in all cases. For example during clinical electrophysiologic (EP) study, in which the clinician endeavors to determine the target site to ablate the heart in the patient, it is attempted to initiate ventricular tachycardia by electrical stimulation. If tachycardia cannot be initiated, the former method described in the U.S. Pat. No. 6,236,883 to Ciaccio et al will not work because the methodology requires signals obtained from the heart surface during ventricular tachycardia. Furthermore, sometimes tachycardia can be initiated but there is poor hemodynamic tolerance, which means that the pumping of blood is so poor during the tachycardia that the doctor must terminate it so that the patient does not experience syncope. The method of the present disclosure addresses both problems.

In one embodiment of the present disclosure, the reentry isthmus may be localized and its shape may be estimated based on sinus-rhythm signals from the heart surface. Sinus-rhythm is the normal rhythm of the heart. Therefore, based on this methodology there may no longer be a need to induce ventricular tachycardia in the patient's heart during clinical EP study.

The method of the present disclosure provides the clinician with a target area to ablate the heart to stop reentrant ventricular tachycardia from recurring. Accuracy is important so that only those portions of the heart at which ablation is needed are actually ablated. Ablating other areas can increase the chance of patient morbidity, by damaging regions of the heart unnecessarily. Also, there is less chance that the patient will be required to have a repeat visit, which will reduce cost of the total procedure and reduce discomfort to the patient. Rapidity is important to reduce the amount of fluoroscopy time and therefore reduce the radiation exposure to the patient, as well as cost due to the reduction in time for the procedure, and patient discomfort.

The method of the present disclosure is also an advance over previous methods because there may be no need to acquire many signals directly from the heart surface which is difficult and time consuming, for the procedure. Instead, only the electrocardiogram (ECG) signal may be needed during tachycardia. This ECG signal may be obtained during the EP study, or even via a Holter Monitor when the patient is ambulatory and the heart undergoes an episode of tachycardia. Therefore, the method of the present disclosure may greatly improve the accuracy of targeting the best ablation site to stop reentrant ventricular tachycardia even when tachycardia cannot be induced or is hemodynamically stable, both of which occur in a significant number of patients.

Treatment of reentrant ventricular tachycardia by catheter ablation methods is hampered by the difficulty in localizing the circuit, particularly when the circuit structure is complex, the tachycardia is short-lived, or when reentry is not inducible during electrophysiologic study [1]. If measurements of sinus rhythm activation could be used to accurately localize reentry circuit features, it could potentially greatly improve the cure rate under these circumstances. A number of clinical and experimental studies to determine the usefulness of sinus rhythm parameters for targeting reentry circuits have been reported. The time of latest depolarization during sinus rhythm has been partially correlated to the location of the reentry isthmus; however, the relationship is inexact [2–3]. At the border zone, both normal and abnormal (low-amplitude, fractionated, or wide-deflection) electrograms are present [2–5]; however, these abnormal electrograms can be present both within and away from the reentry circuit location and are therefore not a specific predictor of its position in the border zone. Therefore, methods for detection and measurement of abnormal sinus rhythm activation characteristics are not presently sufficient for targeting reentry circuits for catheter ablation, although presence of abnormality suggests the proximity of arrhythmogenic substrate.

When a reentrant circuit can be induced in the infarct border zone by programmed electrical stimulation in a canine model [6], the area where the isthmus forms has at least two conspicuous substrate properties: 1) it is the thinnest surviving cell layer of any area of the border zone [6–7], and 2) there is disarray of gap-junctional intercellular connections which extends the full thickness from the infarct to the surface of the heart [8]. Since these substrate properties persist regardless of rhythm type, they may affect electrical conduction at the isthmus area during sinus rhythm. The hypothesis that these phenomena could be quantified and used to predict reentry inducibility, and isthmus location and shape, when it occurs, was tested in this study.

SUMMARY OF THE INVENTION

This invention provides a method for identifying and localizing a reentrant circuit isthmus in a heart of a subject during sinus rhythm, comprising the steps of: a) receiving electrogram signals from the heart during sinus rhythm via electrodes; b) creating a map based on the received electrogram signals; c) determining, based on the map, a location of the reentrant circuit isthmus in the heart; and d) displaying the location of the reentrant circuit isthmus.

This invention provides a method for identifying and localizing a reentrant circuit isthmus in a heart of a subject during sinus rhythm, comprising the steps of: a) receiving electrogram signals from the heart during sinus rhythm via electrodes; b) creating a map based on the received electrogram signals; c) finding a center reference activation location on the map; d) defining measurement vectors originating from the center reference activation location; e) selecting from the measurement vectors a primary vector indicating a location of the reentrant circuit isthmus in the heart; and f) displaying the location of the reentrant circuit isthmus.

This invention provides a system for identifying and localizing a reentrant circuit isthmus in a heart of a subject during sinus rhythm, comprising: a) an interface for receiving electrogram signals from the heart during sinus rhythm via electrodes; b) processing means for creating a map based on the received electrogram signals, and determining, based on the map, a location of the reentrant circuit isthmus in the heart; c) a display adapted to display the location of the reentrant circuit isthmus.

This invention provides a system for identifying and localizing a reentrant circuit isthmus in a heart of a subject during sinus rhythm, comprising: a) receiving means for receiving electrogram signals from the heart during sinus rhythm via electrodes; b) storage means for storing electrogram data corresponding to the electrogram signals received by the receiving means; c) processing means for retrieving the electrogram data, creating a map based on the electrogram signals, finding a center reference activation location on the map, defining measurement vectors originating from the center reference activation location, selecting from the measurement vectors a primary axis vector indicating a location of the reentrant circuit isthmus in the heart, finding threshold points of the electrogram signals on the map, and connecting the threshold points to form a polygon indicating a shape of the reentrant circuit isthmus in the heart; and d) a display for displaying one of the location and shape of the reentrant circuit isthmus.

BRIEF DESCRIPTION OF THE FIGURES

FIGS. 1A–1C are activation maps of the reentrant circuit. At the four margins of the map are indicated their respective locations on the heart: the left anterior descending coronary (LAD), the base, lateral left ventricle (LAT), and apex. The small numbers in boxes are activation times at each of the recording sites. Isochrones are labeled with larger numbers in boxes. Circles containing ray numbers are referred to in the text. The shaded area represents the place where the double loop merges during reentry (called the central common pathway or reentry isthmus). A table in FIG. 1A contains ray numbers as well as the results of linear regression analysis along each ray. For each ray numbered 1–8, the columns of the table show the slope of the regression line, termed the activation gradient (AG), and linear regression coefficient ($r^2$) values, termed the activation uniformity (AU). Thick black lines designate regions of conduction block. Arrows show the direction of wavefront propagation. FIG. 1D shows an electrogram duration map for the sinus-rhythm cycle of FIG. 1A. The locations of the reentry arcs of block from the activation map of FIG. 1C are shown overlapped as thick black lines. Between the arcs of block is the actual location of the reentry isthmus. The estimated isthmus location, determined by activation and electrogram duration analysis, is inscribed by the small circles on the map. The estimated area approximately overlaps the shape of the actual reentry isthmus.

FIGS. 3A–3B show a database, represented as a scatter plot, and one and two-dimensional boundary lines for classification of the primary vector parameters of activation gradient (AG) and activation uniformity (AU) according to one embodiment of the present disclosure. In both FIGS. 3A and 3B, the dotted line shows the best boundary-line to classify those cases in which reentry may occur versus those cases in which reentry may not occur based on the sinus-rhythm activation gradient parameter. The boundary line separates most of the cases in which long-runs of monomorphic reentry could be induced (solid circles) to the left side of the plot, and most of the cases in which reentry was not inducible (open circles) to the right side of the plot, in both panels. For cases in which only short-runs of reentry were inducible (triangles), many of the points resided to the left of the line, i.e. it was correctly classified for these cases that reentrant ventricular tachycardia would occur. In FIG. 3A, the dashed line denotes the best two-dimensional boundary to separate cases in which reentrant ventricular tachycardia would versus would not be inducible based on the sinus-rhythm activation gradient and uniformity. This two-dimensional classification boundary improved classification by correctly adding two more open circles (no reentry occurred) to the right side of the boundary-line. In FIG. 3B, the same procedure is used, with the same result, except that the parameters were the mean electrogram duration and the activation gradient.

FIGS. 4A–4Y are estimated isthmus parameters experiments with long-runs of reentry. The actual reentry isthmus is the area between the arcs of block denoted by thick curvy black lines. The estimated reentry isthmus derived from electrogram duration and activation analysis is denoted by the cross-hatched area. The estimated and actual reentry isthmuses often coincide. The location and direction of the primary axis determined from activation mapping is denoted by the arrow in each panel, and in most cases it approximately aligns with the long-axis (i.e., entrance to exit direction) of the reentry isthmus. The dashed line denotes the estimated best ablation line.

FIGS. 5A–5K are estimated isthmus parameters experiments with short-runs of reentry. FIGS. 5A–5E are taken during polymorphic tachycardia where the electrocardiogram or ECG is irregular in period and/or shape of the signal. FIGS. 5F–5K were taken during monomorphic tachycardia where the electrocardiogram or ECG is regular in period and in shape of the signal. These panels are the same as for the panels of FIG. 4 except that these cases included only short-runs, for example, less than 10 heartbeats of ventricular tachycardia. The method produces good overlap of estimated with actual reentry isthmus for most of the monomorphic cases; however, the overlap is less satisfactory for polymorphic cases because these usually involve the occurrence of multiple reentry isthmuses simultaneously in the infarct border zone.

FIGS. 8A–8D show maps according to one embodiment of the present disclosure. In this figure the activation maps of the endocardial surface during ventricular tachycardia are shown for four different patients. The thick black curvy lines denote arcs of conduction block, and the thinner curvy lines are isochrones of equal activation time, which are labeled. In FIG. 8A (patient 1), the wavefront proceeds between arcs of block at two areas. At the left of the map it crosses the area between the arcs of block at a time of approximately 100 milliseconds, and proceeds upward. At the right side of the map the activation wavefront crosses the area between the arcs of block at a time of approximately 0 milliseconds and proceeds downward. Two distinct wavefronts from the left and right sides of the map coalesce at the center at time approximately 200 milliseconds. The process of the wavefronts looping around the arcs of conduction block rapidly and once each cardiac-cycle is known as reentry. The cycle-length of reentry for patient 1 is approximately 333 milliseconds. (The last isochrone, 333 milliseconds, is written as 0 milliseconds in the map.) In FIGS. 8B–8D (patients 6, 7, and 9) distinctive wavefronts similar course around arcs of conduction block once each cardiac-cycle.

In FIG. 9A is shown the sinus-rhythm activation map. The area of last activation is marked and proceeding from it are eight measurements vectors. The linear regression resulting from each measurement vector is shown in the accompanying table. The vector with greatest activation uniformity and low activation gradient is ray 2 and it is in-spec. Hence ray 2 is the primary axis. The location of the primary axis is expected to coincide with the location of the reentrant circuit isthmus and the direction of the primary axis denotes the predicted direction of the reentrant wavefront as it passes through the isthmus during tachycardia. In FIG. 9B is shown the electrogram duration map. Around the last-activating region of sinus-rhythm and the primary axis so formed (not shown), points with differences in sinus-rhythm electrogram duration between recording sites of, for example, >15 milliseconds, are denoted by circles. These circles on the computerized map grid are connected to for the polygonal surface that is the estimated location and shape of the reentrant circuit isthmus. The estimated best line to ablate, which bisects the estimated isthmus into regions with equal surface area, is denoted by the dashed line and it is perpendicular to the primary axis (measurement vector 2 in FIG. 9A) To the left of FIG. 9B, examples of electrograms in regions with differing sinus-rhythm electrogram duration are shown. When electrogram duration is long, the deflections occur for a longer time during each cardiac-cycle. In FIG. 9C is shown the activation map during pacing. Note that the areas of last activation during pacing coincide with region with long sinus-rhythm electrogram duration. This may be a direct result of the properties of the tissue (poorer conduction in regions of long sinus-rhythm electrogram duration when cycle-length is shorter as it is during pacing). In FIG. 9D, the activation map during tachycardia is shown. There is a reentrant circuit, and it occurs precisely as predicted from the sinus-rhythm electrogram analyses. Ablating along the line denoted in FIG. 9B would cause reentrant ventricular tachycardia to cease because the electrical impulse would be blocked as it traversed the actual isthmus area (FIG. 9D).

FIG. 10 shows estimated isthmuses according to one embodiment of the present disclosure. In the next figure are shown the estimated isthmuses from sinus-rhythm electrogram analyses (dashed lines) and best lines to ablate (dotted lines), and the actual isthmuses determined from activation mapping during ventricular tachycardia (gray areas bordered by thick black curvy lines which denote locations of the actual arcs of conduction block), for the 11 patients of the clinical study. The arrows denote the location and direction of the primary axis. In each case, there is agreement between the estimated and actual isthmus of the reentrant circuit. In many of the cases, ablating along the estimated best line, plus, for example, 10% more in each direction, would cause the electrical impulse to be blocked within the actual reentrant circuit isthmus; hence reentrant ventricular tachycardia would cease. In each case, the best estimated ablation line ablates little more of the heart than is necessary, hence minimizing the chance of patient morbidity as a result of the ablation procedure.

FIG. 12 shows a table of Patient Clinical Data. The patient number, sex, infarct location, time from myocardial infarct to EP study, drug therapy, and VT cycle length at onset are given.

DETAILED DESCRIPTION OF THE INVENTION

Figures 1A, 1B, 1C, 1D:
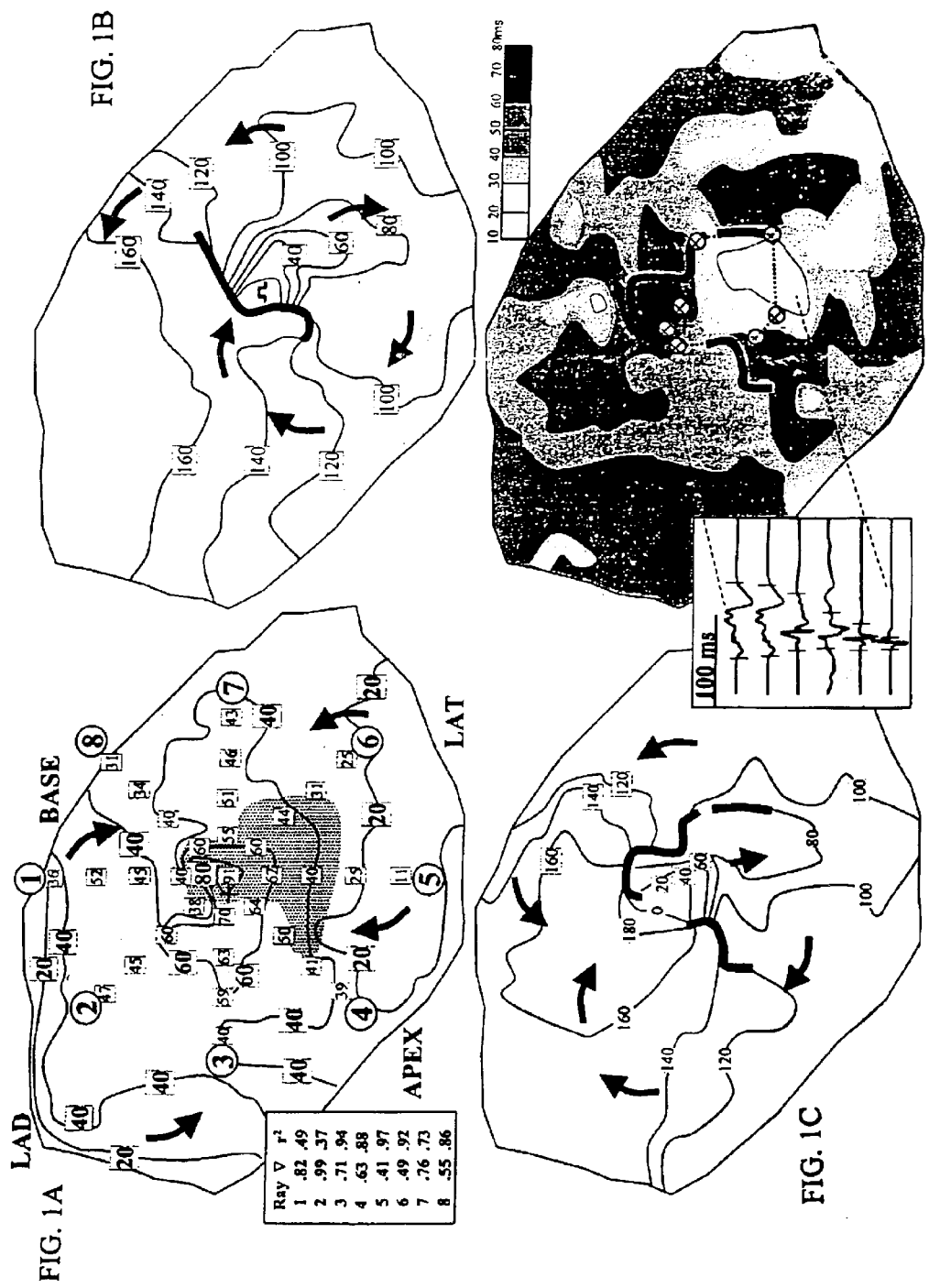
FIGS. 1A–1D are maps of a heart experiencing ventricular tachycardia in which long-runs of monomorphic reentry were inducible by center pacing.

This invention provides a method for identifying and localizing a reentrant circuit isthmus in a heart of a subject during sinus rhythm, comprising the steps of: a) receiving electrogram signals from the heart during sinus rhythm via electrodes; b) creating a map based on the received electrogram signals; c) determining, based on the map, a location of the reentrant circuit isthmus in the heart; and d) displaying the location of the reentrant circuit isthmus.

In one embodiment of the above method, step b) includes arranging activation times of the received electrogram signals based on a position of the respective electrodes.

In one embodiment of the above method, the activation times are measured from a predetermined start time until reception of a predetermined electrogram signal.

In one embodiment of the above method, the map includes isochrones for identifying electrogram signals having activation times within a predetermined range.

In one embodiment of the above method, step c) includes finding a center reference activation location on the map by averaging an electrode coordinate position of a predetermined number of electrogram signals selected based on an activation time.

In one embodiment of the above method, step c) includes defining measurement vectors originating from the center reference activation location and extending outward on the map, the measurement vectors used to designate the electrodes located along the measurement vectors.

In one embodiment of the above method, the electrodes assigned to a measurement vector are chosen according to a distance from the measurement vector. In one embodiment of the above method, the electrodes assigned to a measurement vector are a subset of the electrodes chosen according to a distance from the measurement vector.

In one embodiment of the above method, step c) includes selecting from the measurement vectors a primary axis vector having one of an activation gradient value within a predetermined range and a highest activation uniformity value within a predetermined range and where the primary axis vector indicates a location of the reentrant circuit isthmus.

In one embodiment of the above method, the activation uniformity value is a coefficient of linear regression. In one embodiment of the above method, the activation uniformity value is a coefficient of non-linear regression. In one embodiment of the above method, the activation uniformity value is a variance in activation times along a selected measurement vector. In one embodiment of the above method, the activation uniformity value is a measure of variability along a selected measurement vector.

In one embodiment of the above method, the activation gradient value is a slope of a linear regression line.

In one embodiment of the above method, the activation gradient value is a slope of a non-linear regression line. In one embodiment of the above method, the activation gradient value is a mean absolute difference in activation times along a selected measurement vector. In one embodiment of the above method, the activation gradient value is a difference along the measurement vector In one embodiment of the above method, step c) includes, when a primary axis vector is not found, finding an alternate center reference activation location on the map by averaging an electrode coordinate position of a predetermined number of electrogram signals having an alternate characteristic, defining measurement vectors originating from the alternate center reference activation location and extending outward on the map, the measurement vectors used to designate the electrodes located along the vectors, and selecting from the measurement vectors a primary axis vector having one of an activation gradient value within a predetermined range and a highest activation uniformity value within a predetermined range.

In one embodiment of the above method, step d) includes when a primary axis vector is not found, selecting from the measurement vectors a primary axis vector having one of an activation uniformity value within a predetermined range and a highest gradient value within a predetermined range.

In one embodiment of the above method, the above method further comprises the steps of: e) determining, based on the map, a shape of the reentrant circuit isthmus in the heart; and f) displaying the shape of the reentrant circuit isthmus.

In one embodiment of the above method, step b) includes generating duration values representing a time difference between a starting point and a stopping point in the electrogram signals.

In one embodiment of the above method, the one of the starting point and stopping point is computed to be when an amplitude of the electrogram signal is within a predetermined amount of an amplitude of the electrogram signal.

In one embodiment of the above method, step e) includes finding threshold points in which the difference in electrogram duration values between adjacent sites is greater than a predetermined time interval.

In one embodiment of the above method, step e) includes connecting the threshold points to form a polygon encompassing the center reference activation location.

In one embodiment of the above method, step e) includes connecting the threshold points to form a polygon encompassing the center reference activation location and a predetermined portion of the primary axis vector and indicating a shape of the reentrant circuit isthmus in the heart.

In one embodiment of the above method, the above method further comprises the steps of: g) determining an ablation line to ablate the heart based on the location of the reentrant circuit isthmus; and h) displaying the ablation line.

In one embodiment of the above method, step g) includes drawing the ablation line on the map bisecting the polygon and at a predetermined angle with respect to the primary axis vector.

In one embodiment of the above method, the ablation line traverses the polygon plus a predetermined distance.

This invention provides a method for identifying and localizing a reentrant circuit isthmus in a heart of a subject during sinus rhythm, comprising the steps of: a) receiving electrogram signals from the heart during sinus rhythm via electrodes; b) creating a map based on the received electrogram signals; c) finding a center reference activation location on the map; d) defining measurement vectors originating from the center reference activation location; e) selecting from the measurement vectors a primary vector indicating a location of the reentrant circuit isthmus in the heart; and f) displaying the location of the reentrant circuit isthmus.

In one embodiment of the above method, the above method further comprises the steps of: g)finding threshold points of the electrogram signals on the map; h) connecting the threshold points to form a polygon indicating a shape of the reentrant circuit isthmus in the heart; and i) displaying the shape of the reentrant circuit isthmus.

In one embodiment of the above method, the above method further comprises the steps of: j) finding an ablation line based on the polygon; and k) displaying the ablation line.

This invention provides a system for identifying and localizing a reentrant circuit isthmus in a heart of a subject during sinus rhythm, comprising: a) an interface for receiving electrogram signals from the heart during sinus rhythm via electrodes; b) processing means for creating a map based on the received electrogram signals, and determining, based on the map, a location of the reentrant circuit isthmus in the heart; c) a display adapted to display the location of the reentrant circuit isthmus.

This invention provides a system for identifying and localizing a reentrant circuit isthmus in a heart of a subject during sinus rhythm, comprising: a) receiving means for receiving electrogram signals from the heart during sinus rhythm via electrodes; b) storage means for storing electrogram data corresponding to the electrogram signals received by the receiving means; c) processing means for retrieving the electrogram data, creating a map based on the electrogram signals, finding a center reference activation location on the map, defining measurement vectors originating from the center reference activation location, selecting from the measurement vectors a primary axis vector indicating a location of the reentrant circuit isthmus in the heart, finding threshold points of the electrogram signals on the map, and connecting the threshold points to form a polygon indicating a shape of the reentrant circuit isthmus in the heart; and d) a display for displaying one of the location and shape of the reentrant circuit isthmus.

The method of the present disclosure is used to target ablation sites on the surface of the heart to stop reentrant ventricular tachycardia from occurring. It may be used to target sites on either the endocardial or the epicardial surface of the heart. One embodiment of the present disclosure involves using signals acquired during sinus-rhythm, where sinus rhythm is the normal rhythm of the heart. These signals may be acquired during clinical electrophysiologic EP study with special equipment designed for this purpose. Several types of catheters are available for this purpose when the reentrant ventricular tachycardia is believed to be endocardial in origin. When reentrant ventricular tachycardia is believed to be epicardial in origin, open chest surgery or other procedures may be required to obtain signals and map conduction on the surface. The type of catheter may influence the data acquisition method.

For example, in a noncontact clinical system, the probe does not contact the heart surface, signals may be acquired and by a mathematical inverse equation, the signals that would occur on the heart surface may be reconstructed. When a standard clinical catheter is used, the catheter may acquire signals from, for example, two adjacent locations at once, because there are two recording electrodes on the catheter, and those electrodes are located close together. Data may be recorded over one heartbeat during sinus-rhythm, and/or one heartbeat during ventricular tachycardia (and its cycle-length). Once the data signals are obtained, they are then analyzed according to the procedures described further in the present disclosure.

The present disclosure can be incorporated into existing clinical methodology for catheter ablation for example, as a computer software algorithm, or as a standalone computerized data acquisition and analysis system that may be implemented, for example, as in software residing on a digital computer, or in hardware components, for example, a specially designed integrated circuit or circuits for maximum speed of processing. The target ablation area, with relevant quantitative values, may be output to a display, for example, a CRT monitor, so that the clinician may rapidly make use of the information and guide the catheter or other ablation device. Alternatively, the target ablation area and other relevant values may be output in printed or other auditory, visual or tactile form.

Figure 13:
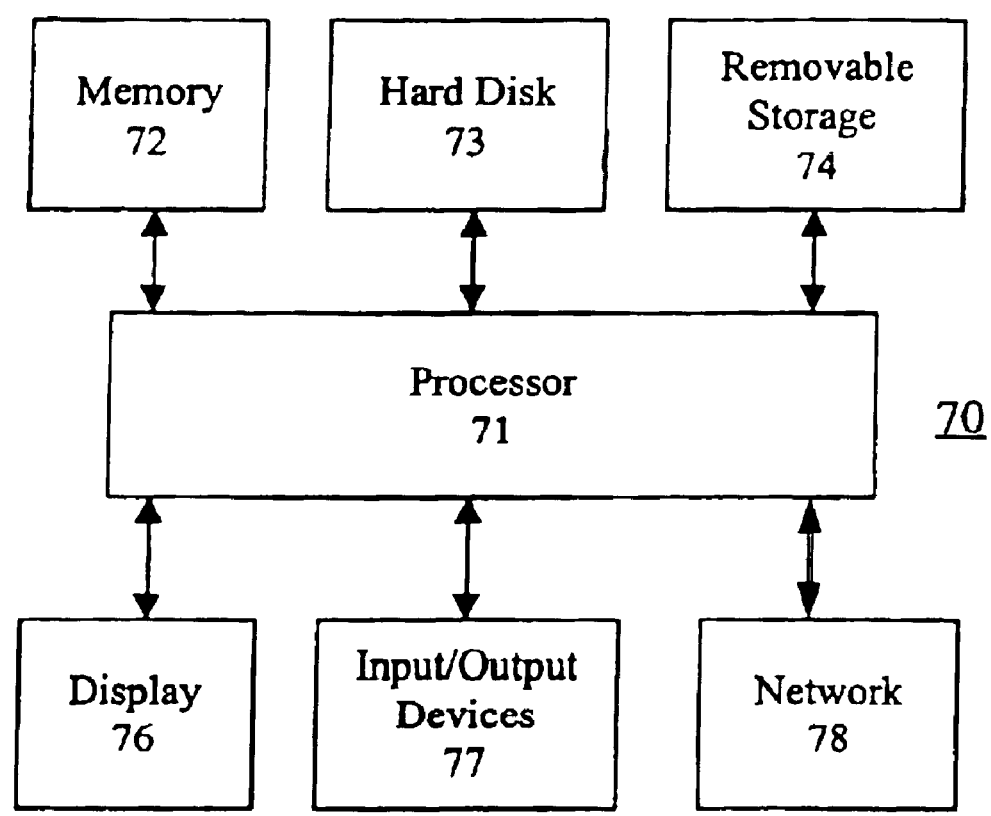
FIG. 13 shows a diagram of a system according to an embodiment of the present disclosure.

FIG. 13 is a diagram of a system according to an embodiment of the present disclosure. FIG. 14 shows a computer system 70, which may include a processor 71. The computer system may include a memory 72, for example, random access memory (RAM), a hard disk 73, and a removable storage 74, for example a CD-ROM drive. The memory 72, hard disk 73 and removable storage 74 may be used for storing, for example, system code, heart signal input data, user input parameters, and patient database values.

The computer system 70 also may include, a display device 76, for example, a CRT or LCD monitor, which may have a touch screen display for input, a speaker, and a projection display. The computer system 70 may also include input/output devices 77, for example a keyboard, mouse, light pen, tactile control equipment, microphone, printer, scanner, electrodes, catheter and other input devices. The computer system 70 may also include a network interface 78, for example, a wired or wireless Ethernet card, for connecting to a network for communication with other electronic equipment. Such a computer system 70 may be a personal computer, laptop or other portable computing device or may be a standalone system.

In one embodiment of the present disclosure the output may include a series of maps that show, the sinus-rhythm activation characteristics in the infarct border zone, the sinus-rhythm electrogram duration characteristics in the infarct border zone, the location of the estimated reentry isthmus in the infarct border zone, and the location of the estimated best ablation line in the infarct border zone. These maps may include numerical coordinates used to guide the clinician as to the correct placement of the catheter to ablate the heart.

Other information may be output, including, for example, activation maps of reentrant ventricular tachycardia, for example, if such is available, to confirm the computer selection of the target ablation area and provide additional information to the clinician in order to modify the suggested ablation site if necessary.

The measurement vectors in the XY space of the activation map are used to define which sites are included in the analysis of activation times. The regression line is a line having as one dimension, the distance along that measurement vector for which the particular regression was calculated, and as the other, the values of the activation times along the measurement vector at each site.

FIGS. 3A–3B show database entries depicted as a scatter plot, and one and two-dimensional boundary lines (dotted and dashed respectively) for classification of the primary vector parameters of activation gradient (AG) and activation uniformity (AU) so that it may be predicted whether the patient ventricular tachycardia is due to a reentrant circuit at the recording surface. Either line is used separately for classification purposes. In FIGS. 3A–3B, the solid circles denote experiments in which monomorphic reentrant ventricular tachycardia occurred. The open circles denote experiments in which reentrant ventricular tachycardia did not occur. The triangles denote experiments in which reentrant ventricular tachycardia occurred but is was due to a polymorphic tachycardia. The latter may be the most difficult to classify.

In the top panel FIG. 3A is shown the relationship between AG and AU for data obtained in approximately 50 canine experiments. Although the canine heart model is not precisely the same as reentrant ventricular tachycardia in humans, there is a close correspondence and hence the scatter plot data serves as a model or guide for human patients. Each point represents the AU and AG of a primary vector from each canine experiment in the two-dimensional (XY) space. The lines drawn in the scatter plot denote the best one-dimensional (vertical line) and two-dimensional (horizontal line) boundaries for classifying those canine hearts in which it is predicted that reentrant ventricular tachycardia will occur at the recording surface versus those in which it is predicted not to occur. For the canine experiments whose AG/AU point is plotted to the left of the lines, reentry is predicted to occur.

For the canine experiments whose AG/AU point is plotted to the right of the lines, reentry is predicted not to occur at the recording surface. In such cases where reentrant ventricular tachycardia is predicted not to occur at the recording surface, it may still occur at the opposite surface of the heart or in the interior of the heart. For example, recordings were made in the canine heart along the epicardial surface. Reentry may occur at the endocardial surface in these cases. Ventricular tachycardia in some of these experiments may be caused by a focal point rather than a reentry loop. Such information is highly important to the clinician during ablation therapy.

In FIG. 3B, the parameters used are the activation gradient and the electrogram duration. Similar results as those of FIG. 3A are obtained. The parameters can be used to predict whether or not reentrant ventricular tachycardia will occur with the same accuracy as in the top panel. In both the top and the bottom panels, the activation gradient (AG) alone is a good classifier of whether or not reentrant ventricular tachycardia will occur, as can be seen by the vertical line (one-dimensional boundary) in each panel. In contrast, the activation uniformity (AU) of the top panel, Y axis, and the electrogram duration of the bottom panel, Y axis, alone would not be good classifiers, for example, a one-dimensional boundary or line in the horizontal direction, may not provide a good classifier either in the top or bottom panel.

Figure 6:
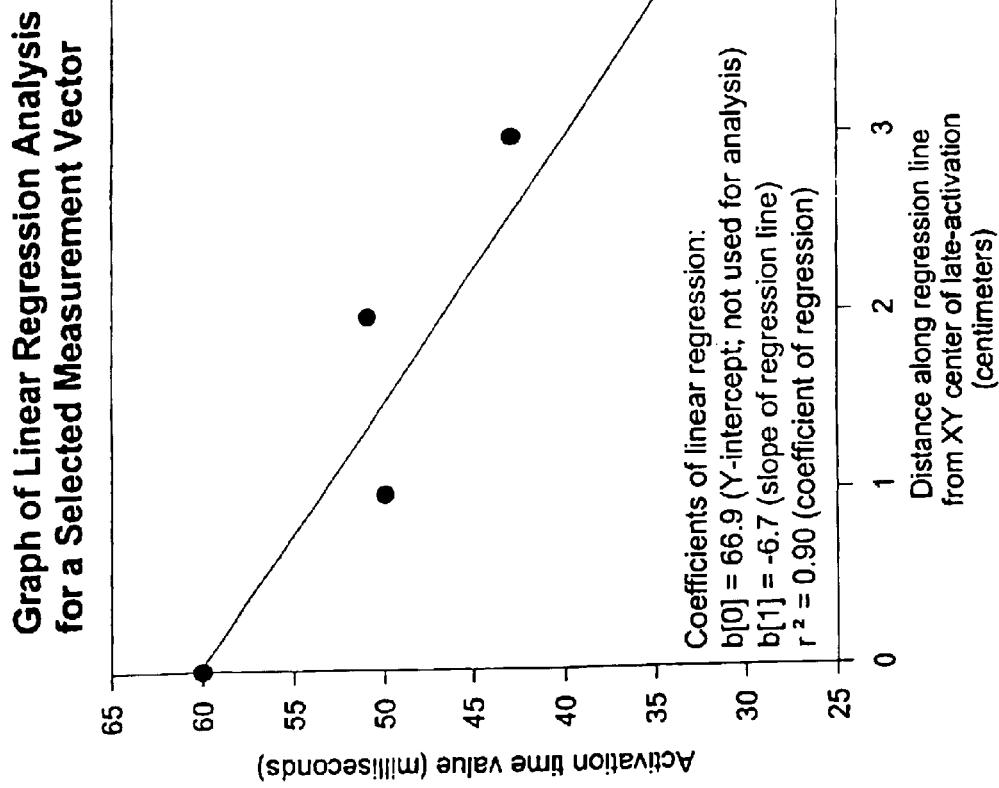
FIG. 6 is a regression line diagram according to one embodiment of the present disclosure.

FIG. 6 shows a sample regression line diagram according to one embodiment of the present disclosure. The axes are the distance along the measurement vector (X-axis) and the activation time at the recording site located at each distance (Y-axis). There are 5 points which is the number of values used for the experimental study of Ciaccio et al, Jul. 31, 2001, and for the clinical study of Ciaccio et al submitted. For regression analysis, a minimum number of points, for example, 5, may be used. The line in the graph is the regression line, which is the line at which the mean distance to the points is minimized based on the least-squares error criterion. The closer the fit of the points to the line, the higher the coefficient of linear regression ($r^2$ value or linearity) and therefore the higher the activation uniformity. The highest uniformity is when all of the points reside on the line (perfect linearity or $r^2=1.0$). The poorer the fit of the points to the line, the lower the coefficient of linear regression and therefore the lower the activation uniformity. The lowest uniformity is when all of the points are randomly scattered (no linearity or $r^2=0.0$).

Figure 7:
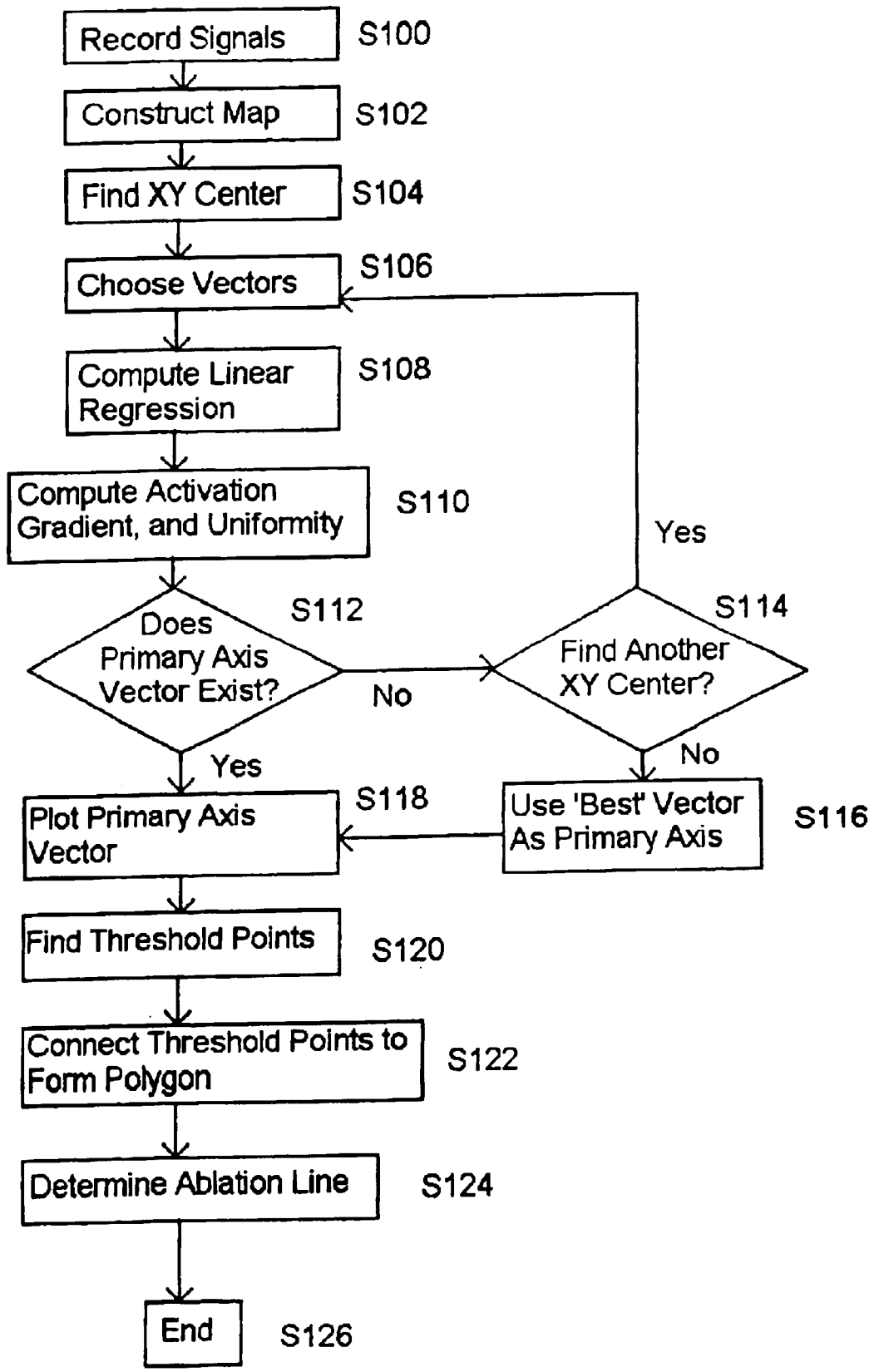
FIG. 7 is a flowchart according to one embodiment of the present disclosure.

FIG. 7A provides a flow chart diagram of one embodiment of the method according to the present disclosure. In Step S100, a catheter may be positioned within the left ventricular chamber of the heart during sinus-rhythm, and electric measurement signals may be recorded from throughout the surface of the heart at different recording sites during sinus-rhythm using a catheter attached to a data acquisition device. As described above, if a noncontact probe or electrode array is used, for example, a basket catheter, these recording measurements may be made simultaneously. If a standard ablation catheter with two electrodes is used, the recoding measurements may be made in turns.

Once the measurement signals are received, an activation map (FIG. 1A) and an electrogram duration map (FIG. 1D) may be constructed based on the recorded signals in Step S102. In this step, the measurements may be mapped from the recording sites onto their respective portions of the heart.

In Step S104, based on the activation map, the last-activating region XY center, shown by the cross-hair in FIGS. 1A, 1D, 2A, and 2D, may be determined by comparing the activation times of the recorded sites, and the method may select a number of sites in a region having latest activation times. The latest activation region may include, for example, a contiguous region of five or more sites.

To determine which recording sites may be used for analysis, first the XY center of last activation is determined. Then the measurement vectors may be positioned with the hub at the XY center. Along these measurement vectors may be marks, for example, at some equal spacing 1 centimeter apart. For each mark, the recording site which is closest to it in the XY directions may be chosen as the site whose activation time is used as the measurement value for that point. This may be done for marks along each measurement vector, for example, for 5 marks. When the activation times to be used for analysis have been determined, the linear regression of these times may be computed according as shown, for example, in FIG. 6, which shows a plot of the linear regression line.

The last-activating region XY center is determined and, in Step S106, vectors may be chosen with origins at the last-activating region XY center. In one embodiment of the present disclosure, vectors may be chosen, for example, as 8 vectors separated by a difference in orientation of 45 degrees with one vector oriented directly vertical in the map. Activation times may then be determined along the vectors originating from the XY center.

In Step S108, linear regression is computed for the times along each vector. Linear regression assumes an association between the independent and dependent variable that, when graphed on a Cartesian coordinate system, produces a straight line. Linear regression finds the straight line that most closely describes, or predicts, the value of the dependent variable, given the observed value of the independent variable. The equation used for a Simple Linear Regression is the equation for a straight line, where y is the dependent variable, x is the independent variable, b0 is the intercept, or constant term (value of the dependent variable when x=0, the point where the regression line intersects the y axis), and b1 is the slope, or regression coefficient (increase in the value of y per unit increase in x). As the values for x increase, the corresponding value for y either increases or decreases by b1, depending on the sign of b1.

Linear Regression is a parametric test, that is, for a given independent variable value, the possible values for the dependent variable are assumed to be normally distributed with constant variance around the regression line. Linear regression routines work by finding the best fit straight line through the data points. By "best fit" it is meant that the line is optimally positioned, based an error criterion, so that the mean distance to all the points on the graph is minimized. The error criterion used is called the least squares error, or sum of the distances from each point to the point on the line that forms a perpendicular angle.

In step S110, the activation gradient (AG) and uniformity (AU) which are, respectively, the slope of the regression line and the coefficient of linear regression, are determined from the activation times along each vector. The slope of the linear regression line is the value $b_1$ in the equation for a straight line: $y=b_1 x+b_0$.

In step S112, the method of the present disclosure searches for a primary axis vector. The primary axis vector is the vector with activation gradient and uniformity within a specified range, for example, the vector with steepest gradient and greatest uniformity if more than one vector have parameters in range. The steepest gradient is that in which there is the largest change in activation time per unit distance along the vector, for example, $\Delta t/\Delta x$ is maximized, where t is the activation time and x is the distance along the measurement vector. When the slopes are negative, this means the largest negative gradient, because larger negative numbers are steeper, and smaller negative numbers, those closer to zero, are shallower. The conduction velocity is the inverse of the activation gradient, for example, $\Delta x/\Delta t$ and therefore conduction velocity is diminished as the activation gradient increases.

Areas along which the isthmus forms may have diminished sinus-rhythm conduction velocities. The method of the present disclosure may scale $\Delta t/\Delta x$ by a factor of, for example, 1/5 or 0.2, which may represent the distance between recording sites of approximately 5 centimeters. Conduction velocities below, for example, 0.75 meters per second (millimeters per millisecond), may be generally found along the primary axis, which may be converted to activation gradient, 1/(0.75)=4/3=1.33. The scale may be reversed, for example, 1.33/0.2≈6.5, which is the slope of the regression line for a conduction velocity of, for example, 0.75 m/s. Hence, a regression line slope of, for example, −6.5 or steeper (greater negative value) may indicate the conduction velocity is at or below, for example, 0.75 m/s. When conduction velocity falls below about, for example, 0.25 m/s, the area may not be one in which the reentrant circuit isthmus will form. Hence, there may be a range of sinus-rhythm gradients in which reentrant ventricular tachycardia would be expected to occur.

Uniformity is the proximity of the coefficient of linear regression to 1.0. At 1.0, all of the points in the regression plot are on the regression line and there is perfect uniformity of conduction all along the location of the measurement vector. The minimum value that the coefficient of linear regression may have is 0.0 which means that the points in the regression line scatter plot are completely random; there is no uniformity. Higher uniformity means that the individual or local conduction velocities, i.e., the distance between any two sites divided by the distance in activation times between those same sites, become more and more similar from site-to-site among the sites used for analysis along a measurement vector.

If no vector has parameters within range, then no primary axis vector is selected at this time. (No, Step S112) In Step S114, the method of the present disclosure then may search for an XY center of another region with contiguous, late-activation times. If there is an XY center of late-activating region of sinus-rhythm with parameters within range, (Yes, Step S114) then the method returns to Step S106, where vectors are chosen based on the new XY center and the method continues.

The process for searching for any XY center of late-activation may be performed as follows. Determine late sites at which adjacent or neighboring sites activate earlier in time. A late site is a site whose activation time follows that of all neighboring sites. These neighboring sites can be those, for example, closest to it in the vertical, horizontal, and diagonal directions. From the time of a given late site, include in the late-activation area of that late-site those contiguous sites with activation preceding the late site by a predetermined number of milliseconds, for example, 10 milliseconds. If the late site plus the recording sites contiguous with it are greater than some number for example, 5 sites in total, then count the area so formed as one of late-activation. Compute the XY-center as the mean distance in the X and in the Y directions on the computerized map grid for all of the contiguous sites in the late-activation area. Repeat this procedure for all late sites. Of the resulting late-activation regions, determine whether or not a primary axis in-spec, that is, with activation gradient and activation uniformity along the primary axis meeting the more stringent threshold criteria of S112, is present first at the last-activation regions whose late site activates last among all of the late sites. If no measurement vector meets the more stringent threshold criteria of S112, continue this procedure for the last-activation region whose late site activates next-to-last among all of the late sites.

If there is not another XY-center of late activation (No, Step S114), then in Step S116, the vector with steepest gradient within a pre-specified range that is also within a pre-specified range of uniformity may be chosen as the primary axis and the method continues to Step S120.

The more stringent ranges specified in the initial search for a primary axis vector in Step S112 may not be the same as those ranges specified in the subsequent search for a primary axis vector in Step S116. The less stringent ranges used in Step S116 will be a different standard than in Step S112. The standard for S112 may be uniformity $r^2$ between, for example, 0.8 and 1.0, and gradient below, for example, −6.5 to −20 slope of the regression line with conduction velocity between, for example, 0.75 m/s and 0.25 m/s. The standard for S116 may be uniformity $r^2$ between, for example, 0.6 and 1.0, and gradient below, for example, −3.3 to −20 slope of the regression line with conduction velocity between, for example, 1.5 m/s and 0.25 m/s.

If the primary axis vector is within the range of activation gradient and uniformity (Yes, Step S112), then ventricular tachycardia due to a reentrant circuit may be predicted to occur. The primary axis vector is a line that may indicate the approximate location of the reentry isthmus, in the sense that the primary vector overlaps a part of the actual reentry isthmus, and the orientation of the primary vector may be approximately in-line with the actual reentrant circuit isthmus. The primary axis vector may point in the direction from the location where the activating wavefront enters the isthmus to the place where it exits the isthmus.

If the primary axis is not within range (No, Step 112), then ventricular tachycardia due to a reentrant circuit may not be expected to occur. If reentrant ventricular tachycardia is not predicted to occur, then the clinician may be informed through the computer hardware/software that the ventricular tachycardia episodes are not due to a reentrant circuit. The clinician may then modify the diagnostic procedure accordingly.

In another embodiment of the present disclosure, a scatter plot may be used to predict whether ventricular tachycardia will occur at the recording surface for the patient. The scatter-plot is a graphical representation of a data base consisting of the data from previous patients or experimental results which are used as exemplars. The one- and two-dimensional boundary lines are used to classify any new patient (input) for the parameters measured along the primary axis of activation gradient versus activation uniformity (top panel), or activation gradient versus electrogram duration (bottom panel). If the point from the new input resides to the left of the one or the two dimensional line, it is predicted that reentrant ventricular tachycardia will occur at the recording surface for the patient; otherwise not. Either the top panel or the bottom panel may be used for this classification.

If there is no reentry predicted, but there is ventricular tachycardia, one of two possible events may be occurring: ventricular tachycardia is focal (ectopic). These tachycardias may be cured if they can be induced. In this case, from the ventricular tachycardia activation map, the point of first activation is the focus, and the clinician may ablate this point to stop tachycardia (there is no circuit or loop, just a point or focus). In another event, there is reentry, but it is occurring elsewhere in the heart other than the surface (endocardial or epicardial) where recordings are being made. For example, if recordings are made from the endocardium with the catheter, the reentry circuit may be located in the epicardium. If the clinician knows the location of the epicardial circuit, it may be possible to ablate through the heart wall from endocardium to epicardium, using a higher radiofrequency energy, to stop tachycardia. This entails more damage to the heart and therefore more chance of morbidity to the patient.

If a primary axis vector is found (Yes, Step S112) then reentry may be predicted to occur, and in Step S118, the location of the primary axis vector may be plotted on the computerized electrogram duration map.

In Step S120, points are determined where the difference in electrogram duration between adjacent sites may be greater than some threshold, for example, 10–15 milliseconds.

In Step S122, those points may be connected to form a polygonal surface encompassing the XY center of the last-activating region so as to minimize the maximum distance between any two connected points, and minimize the average distance between connected points. The surface area of the polygon may be above a pre-defined threshold, for example, 4 centimeters square. The polygonal surface may encompass, for example, at least the first 1 cm in length of the primary axis that originates from the XY center of the last-activation region. The polygonal surface so formed may be an estimate of the location and shape of the central common pathway (isthmus) of the reentrant circuit.

To connect the points to form the polygonal surface, points on the computerized sinus-rhythm electrogram duration map grid in which the difference in electrogram duration between adjacent sites is greater than, for example, 15 milliseconds, may be marked. The points may be connected to encompass the XY center of late-activation determined from the sinus-rhythm activation map, and also so as to encompass the first, for example, 1 centimeter, of the location of the primary axis from its origin at the XY center of late-activation.

The points that are connected may be adjusted so as to minimize the maximum difference between points. The points that are connected may be adjusted so as to minimize the mean difference between points. The minimum surface area of the polygon formed by connecting the points may be be greater than, for example, 4 centimeters squared ($cm^2$). The polygon so formed may be an estimate of the location and shape of the isthmus of the reentrant circuit that forms during ventricular tachycardia.

In step S124, the estimated ablation line is determined so as to bisect the estimated central common pathway into halves with equal surface areas, or with unequal areas, for example, 25% and 75%. The direction of the ablation line may be perpendicular to the primary axis, where the primary axis approximates the direction of the long-axis of the central common pathway. The length of the estimated ablation line may extend across the estimated central common pathway and may extend further, for example, 10%, to ensure the central common pathway is ablated across its entirety.

In another embodiment, the method of the present disclosure may determine whether ventricular tachycardia is due to reentry by plotting the activation gradient and uniformity of the primary axis in a scatter plot with points, for example, from other tachycardias from other patients that were used for learning (exemplars), as shown, for example in FIGS. 3A and 3B. Based on the location of the new point on either side of the linear or nonlinear classification boundary, whether or not reentry will occur may be predicted. For example, if the data point of the patient lies to the left of the two-dimensional classification boundary line, reentry may be predicted to occur, else not. In FIG. 3A, two 1-dimensional thresholds were used, and in FIG. 3B, a single 2-dimensional threshold was used for classification.

In the case where no measurement vector meets the most stringent criteria at any late-activating region (No, Step S112), then the reduced stringency criteria may be emplaced in which the best of any of the measurement vectors originating from any of the late-activating centers present may be made the primary vector. In this case, reentry may be predicted not to occur. The AG and AU for this primary vector may be used as a new point in the database for the scatter plot. It may also point to whether the tachycardia may be due to a focus (point source) or whether it may be reentry but located on the other surface of the heart (epicardium versus endocardium).

FIG. 11 shows another example of how electrogram analyses may be used to determine areas of the reentrant ventricular tachycardia circuit. In FIG. 11A is the sinus-rhythm activation map. Shown is an area of late-activation, and the measurement vectors radiating from it, in which one of the vectors meets the stringent criteria for primary axis (vector 8 with AU=0.98 and AG=0.32). Along the primary axis, electrical conduction is slow and uniform during sinus-rhythm. In FIG. 11B is shown the sinus-rhythm electrogram duration map. The numbers denote the electrogram duration in milliseconds for each of the gray levels. In each gray level, the recording sites have electrogram duration in a range around the number associated with the gray level. The shortest electrogram duration occurs at the area where the reentrant ventricular tachycardia isthmus forms, as is most often the case in clinical and experimental cases. Overlapping the electrogram duration map are the locations of the arcs of conduction block that form during reentry (thick curvy black lines) and the unidirectional arc of conduction block location that forms during a premature stimulus. All of the arcs of block partially align with boundaries between areas with disparate sinus-rhythm electrogram duration. The activation map during pacing with a premature stimulus is shown in FIG. 11C.

Figure 11C:
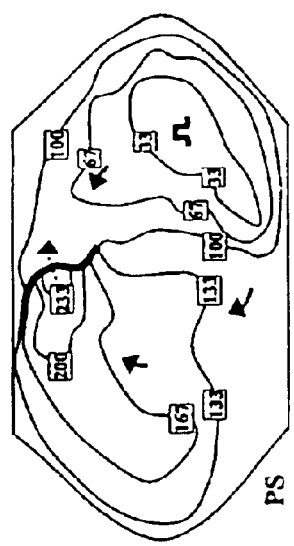
FIGS. 11A–11F show maps according to one embodiment of the present disclosure. In this figure is shown an example of sinus-rhythm electrogram analyses as well as PLATM.
Figure 11B:
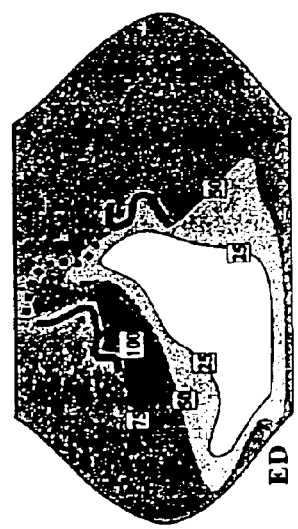
Figure 11A:
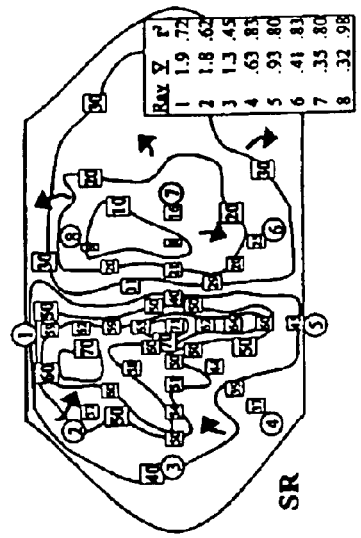
Figure 11F:
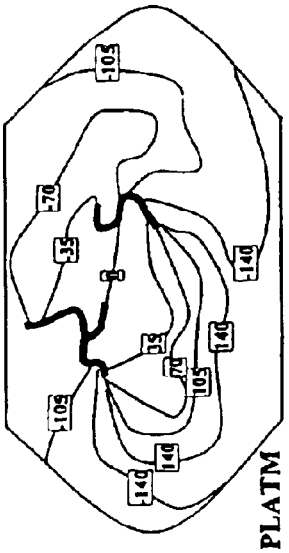
Figure 11E:
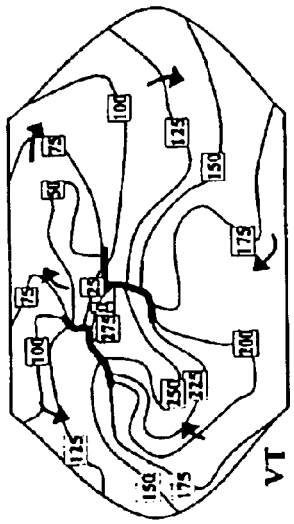
Figure 11D:
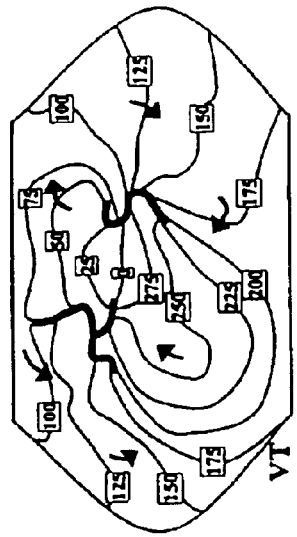

The activation maps during ventricular tachycardia are shown in panels FIGS. 11D–11E. Reentry is shown to occur. Although the arcs of conduction block are functional, and hence shift from cycle-to-cycle as shown from FIG. 11D to FIG. 11E, the general location is unchanged, and the primary axis computed in FIG. 11A still overlies the reentrant circuit isthmus in each case. In FIG. 11F is shown a map made using piecewise linear adaptive template matching (PLATM). These measurements were made during ventricular tachycardia. At each recording site, the PLATM time is the estimated time interval from activation at the local site to activation at the region of the slow conduction zone in the isthmus of the reentrant circuit. Such information is helpful to the clinician during EP study and radio-frequency ablation therapy to "home-in" on the target ablation site with greater clarity even when activation mapping results are unclear. The PLATM map does not rely on activation mapping; hence it can provide a clear picture of where to ablate when activation maps cannot.

FIG. 12 shows a table of Patient Clinical Data. The patient number, sex, infarct location, time from myocardial infarct to EP study, drug therapy, and VT cycle length at onset are given. Most of the patients are male with a median age of approximately 67 years which is in agreement with the national statistics for this malady. As shown in the column, ventricular tachycardia can strike years following the actual myocardial infarct. Various drug therapies are given to control the malady, but rarely are drug regimens a permanent and optimal therapy for ventricular tachycardia. The rapidity of the heartbeat is also shown for ventricular tachycardia in each patient. Faster heartbeat (shorter cycle) general equates with increased discomfort and even injury to the patient during periods in which episodic ventricular tachycardia occurs.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

Animal (canine) studies were first done to develop the methodology and the procedure for analysis [17]. Activation maps were constructed according to the methodology described in the literature, and comparisons were made of activation maps of sinus-rhythm versus reentrant ventricular tachycardia. There were special characteristics that could be observed in the sinus-rhythm activation maps at the location where the isthmus of the reentrant circuit formed during ventricular tachycardia. Namely, the activation wavefront proceeded, during sinus-rhythm, in parallel to but opposite in direction to the activation wavefront during reentry at the location of the isthmus. Also, during sinus-rhythm, activation there appeared to be relatively slow compared with other areas of the infarct border zone, and uniform in terms of a relatively constant conduction velocity and a relatively linear leading edge of the activation wavefront. We believe this is due to the special tissue electrical properties at this location that persist regardless of rhythm type; i.e., full gap-junctional dissociation throughout the thickness of the border zone [8] and having the property of being the area of the border zone with thinnest layer of surviving cells [6, 17]. These properties are believed to produce the observed effects on the activation wavefront during sinus-rhythm, and to set up the conditions for the isthmus of the reentrant circuit to form there (i.e., slow and uniform conduction). It was also observed that adjacent to the area with slow, uniform conduction during sinus-rhythm where the isthmus of the reentrant circuit formed, was the region to last-activate during sinus-rhythm.

To develop a methodology that could quantify the above qualitative observations, mathematical calculations were incorporated to compute the mean of the last region to activate during sinus-rhythm, and to determine the linear regression of activation times along lines (measurement vectors) originating at the XY center of this last-activating region. It was observed that one of the vectors (primary vector or axis with constraints described elsewhere) would always approximately align with the long axis of the isthmus of the reentrant circuit, when it occurred. Hence, it would be possible, based on this methodology of sinus-rhythm measurements: 1. To predict whether or not reentrant ventricular tachycardia would occur. 2. To determine the approximate location of the reentry isthmus, and also the direction of its long-axis.

The methodology was expanded to define the exact shape of the isthmus of the reentrant circuit based on sinus-rhythm measurements [17]. This involved the sinus-rhythm electrogram duration calculation and map constructed from it for all sites in the border zone. Based on the location of the primary vector or axis, when reentry was predicted to occur, sites surrounding this location with a difference in electrogram duration between them that was greater than a predetermined value (15 milliseconds in papers) were marked on the computerized grid. The locations were then connected to encompass the XY location of last-activation (which is always the origin or tail of the primary vector) and a distance along the primary vector (taken as 1 centimeter in the sinus-rhythm paper [17]). The algorithm to connect the points was described elsewhere, and the surface area encompassed by the resulting polygonal shape is the estimated location and shape of the isthmus of the reentrant circuit based on sinus-rhythm measurements. Also described elsewhere, the estimated best line to ablate based on the estimated isthmus location and shape. These procedures were then used successfully on clinical data acquired with a noncontact probe [17].

A) Materials and Methods

A myocardial infarct was created by LAD ligation in experiments in 54 canine hearts and attempts to induce reentry in canines anesthetized with sodium pentobarbitol were made 4–5 days later by premature electrical stimulation [9]. Bipolar electrograms were recorded from 196–312 sites in the epicardial border zone of the anterior left ventricle for 25 experiments with predominantly long-runs of monomorphic reentry (10 beats, mean 181.9 beats), 11 experiments with short monomorphic or polymorphic runs (<10 beats, mean 4.5 beats), and 18 experiments in which reentry was not inducible. Programmed stimulation from the LAD, lateral, base, or center region of the ventricle proceeded using ten S1 stimuli followed by a single premature stimulus. The premature coupling intervals were successively shortened on subsequent stimulus trains until reentry was induced. For consistency between experiments, the multi-electrode array was placed on the heart with the same edge always positioned along the LAD margin. For simplicity, the ventricular area where recording sites in the multi-electrode array were located was considered to encompass the entire infarct border zone.

Activation maps [9] were created from data obtained from the border zone during sinus rhythm, pacing, and reentry, when it occurred. For each experiment, the sinus rhythm map was constructed from an arbitrary cycle at the beginning of the experiment prior to programmed stimulation and pace maps were constructed from cycles of the pace train which led to onset of reentry. Reentry maps were constructed from an early cycle of ventricular tachycardia following stabilization of the circuit (long-runs experiments) or for all cycles (short-runs experiments). Inspection of sinus rhythm activation maps in canine hearts in which reentry was inducible suggested that the isthmus entrance and exit, respectively, tended to form along an axis from the area of last to first activity during sinus rhythm. Moreover, the activating wavefront during sinus rhythm was observed to advance in parallel to this axis, with uniform conduction velocity, and in the opposite direction to activation within the isthmus during reentry. To quantify this phenomenon, the last 10 ms interval during which (5 contiguous sites activated was ascertained. The XY-center of this region was computed as the mean value of the site locations in the X- and Y-directions, referenced to an arbitrary fiduciary point on the computerized electrode grid. The linear regression of activation times was computed along eight rays originating from the geometric center of this last-activating region (45 degree ray separation with orientation such that two of the rays were precisely vertical on the grid). The activation times at four sites along each ray (0.8 cm spacing between sites), plus the center site itself (five sites in all), were used for each regression (rays not entirely on the grid were excluded from analysis). The ray with highest $r^2$ value was termed the primary axis. The regression line slope along the primary axis (termed the activation gradient), and the $r^2$ value (termed the activation uniformity), were graphed for all experiments as a scatter plot. From the scatter plots, the best linear thresholds to classify experiments in which reentry could versus could not be induced were determined manually for the activation uniformity parameter alone and for the activation gradient-uniformity parameters in tandem.

The electrogram duration, defined as that contiguous series of electrogram deflections with no isoelectric segment of >5 ms duration, encompassing the time of local activation at the recording site during one cardiac cycle, was also measured for all electrogram recordings obtained during the same cycle used to construct the sinus rhythm activation map. The starting and ending points, respectively, were considered to be the beginning and ending times at which contiguous electrogram deflections arose above the isoelectric level to an amplitude >10% of the maximum electrogram peak. Electrogram duration for all sites was mapped using the same computerized electrode grid that was used for activation mapping. The location of the XY-center of last-activation during sinus rhythm, and the location of reentry arcs of block determined from the reentry activation map, were superimposed on the electrogram duration map computerized grid. Separate means of electrogram duration were computed for: 1) sites residing along the primary axis that were used for its regression equation, 2) all sites residing within the area where the isthmus formed, and 3) all sites in the border zone (including those within the isthmus). The mean electrogram duration along the primary axis was graphed versus the activation gradient along the primary axis for all experiments, and the resulting scatter plots were also used to classify experiments in which reentry could versus could not be induced as described above for the activation gradient-uniformity scatter plot.

Locations where the difference in sinus rhythm electrogram duration between any two adjacent sites (horizontal, vertical, or diagonal direction) was (15 ms, were marked on the computerized electrogram duration map grid. Selected marks were then connected to form the border of a contiguous region using the following algorithm implemented on a digital PC-type computer: 1. the region must encompass the XY-center of last-activation and the initial 1 cm of the primary axis extending from it, 2. marks were connected so as to: a. minimize the maximum distance between connections, followed by b. minimize the mean distance between connections, and 3. the inscribed region must have surface area (2.0 cm$^2$ (the approximate minimum isthmus surface area that was observed in any experiment). The contiguous region so formed (the estimated isthmus) was compared to the actual location and shape of the reentry isthmus (delineated by connecting the computerized grid locations of block line endpoints which were superimposed from the reentry activation map) and mean(standard error was computed from all experiments. The direction designated by the primary axis was considered to be an approximation of the direction of activation through the actual isthmus during reentry. A straight line, called the estimated line for ablation, was then drawn perpendicular to the primary axis from one edge of the estimated isthmus to the other on the computerized grid. The location of the estimated line for ablation was chosen so as to bisect the estimated isthmus into halves with equal areas. The percent of the width of the actual reentry isthmus that the estimated line for ablation spanned was then computed and tabulated.

Significance of quantitative variables was determined using computerized statistical procedures (SigmaStat, Jandel Scientific) as follows. For comparison of mean activation gradients and mean electrogram durations, the difference in means (t-test) was calculated. For comparison of isthmus locations, first the XY-center of the estimated isthmus was taken as the point along the primary axis 1 cm from the origin. Then the actual reentry isthmus location on the computerized grid was approximated as the mean XY-location of the four endpoints of the two arcs of block which bounded the isthmus. For polymorphic experiments with multiple isthmus locations, the XY-center of the actual isthmus which was closest to the estimate was used for statistical comparison. The linear regression of estimated versus actual XY-centers was then calculated for all reentry experiments. A linear regression was also computed for percent overlap of isthmuses versus heart rate.

B) Results

In FIG. 1 are shown activation maps for sinus rhythm (A), premature stimulation (S2) from the center of the border zone (B), and reentry (C), and the electrogram duration map (D) for a canine experiment in which only long-runs of monomorphic reentry with a single morphology were inducible. Wavefront propagation direction through the isthmus during reentry (C) is oriented in parallel but opposite to propagation in the same region during sinus rhythm (A). During sinus rhythm (A), the 5 or more last sites to activate within a 10 ms interval have activation times between 60–69 ms. Nearest to the XY-center of last-activation (+) is a site which activates at time 91 ms. The locations used to determine the linear regression, which included this site, are denoted by their activation times and the rays are numbered from 1–8. The accompanying table shows activation uniformity and gradient for each ray. The ray with greatest activation uniformity (the primary axis) is ray 1 ($r^2$=0.97). The primary axis has lowest activation gradient (0.41 m/s) and is approximately parallel to the isthmus long axis. The block lines forming during premature stimulation and during reentry partially align between areas of large disparity in sinus rhythm electrogram duration (for simplicity, only reentry arcs of block are superimposed on the electrogram duration map). Based on the isthmus estimation algorithm, boundary points of the estimated isthmus are given by cross-hatched circles (D). This area partially overlaps the actual reentry isthmus whose boundaries are formed by the superimposed arcs of block. Examples of electrograms with differing electrogram duration are shown (insert, D); within most of the reentry isthmus region, electrogram duration was relatively short. Other long-runs experiments had similar properties to FIG. 1. Along the primary axis for all long-runs experiments, mean activation uniformity and gradient was 0.97 (0.01 and 0.67 (0.04 m/s, respectively. The mean sinus rhythm electrogram duration for sites residing within the isthmus area for all experiments was 24.2 (0.4 ms (mean of 18.4(2.2 sites per isthmus) which was significantly lower (p<0.001) than for the border zone as a whole (34.1 (0.7 ms). For most long-runs experiments including that of FIG. 1, wavefront orientation during sinus rhythm was approximately parallel to the primary axis; therefore the activation uniformity and gradient along the primary axis was proportional to conduction uniformity and velocity, respectively, along the same axis.

In FIG. 2 are shown maps from an experiment in which only short-runs of 3–8 beats of monomorphic reentry could be induced. The sinus rhythm activation map (A) shows the region where the isthmus forms (shaded). The primary axis ($r^2$=0.96) approximately aligned with the isthmus long axis and extended from late- to early-depolarizing regions during sinus rhythm (upward vertical direction originating at the larger 50 ms isochrone). For the reentry episode of FIG. 2, activation maps of reentry beats 1–2 were similar (second beat is shown in B). The reentry arcs of block partially align at edges between areas with large disparity in electrogram duration (D). Mostly short-duration sinus rhythm electrograms are present at the reentry isthmus location. On the third reentry cycle, the left arc suddenly shifted inward (dotted in C) to align with a different edge of large disparity in electrogram duration (D). On the next (termination) cycle, the activating wavefront blocked at the narrowest width of the reentry isthmus (not shown). The boundary points of the estimated isthmus are shown (D, hatched circles) and as in FIG. 1, they partially overlap the actual isthmus location. Other monomorphic short-runs experiments had similar properties to FIG. 2. Along the primary axis for all short-runs experiments, mean activation uniformity and gradient was $r^2$=0.94 (.01 and 0.79(0.12 m/s, respectively. Also for all short-runs experiments, mean sinus rhythm electrogram duration at the isthmus location was 22.7 (0.7 ms (mean of 9.9 (2.0 sites per isthmus) which was significantly lower (p<0.05) than for the border zone as a whole (28.8 (0.6 ms).

The mean sinus rhythm electrogram duration throughout the border zone was significantly less in short versus long-runs experiments (p<0.05).

For experiments lacking reentry, activation uniformity and gradient along the primary axis were $r^2$=0.93(0.02 and 1.22(0.08 ms, respectively, and the mean electrogram duration throughout the border zone was 31.3(0.5. In most experiments lacking reentry, the wavefront propagation direction during sinus rhythm did not align with the primary axis.

In FIG. 3A is shown a scatter plot of activation uniformity and gradient along the primary axis during sinus rhythm for each experiment. Shown are the best threshold to classify experiments using activation gradient alone (dotted line), and for activation gradient-uniformity in tandem (dashed line). In 24/25 experiments with long-runs of reentry (solid-circles), and 9/13 primary axes present in 11 short-runs experiments (solid-triangles), each threshold predicted that reentry could be induced. In 15/18 experiments lacking reentry (open-circles), the activation gradient threshold alone predicted that reentry could not be induced; prediction improved to 17/18 when the activation gradient-uniformity threshold was used. The difference in means in the activation gradient parameter between each of the three groups was significant (p<0.001). In FIG. 3B is shown a scatter plot of the mean electrogram duration versus activation gradient computed along the primary axis for each experiment. For comparison the best activation gradient threshold is shown (dotted line; same as in FIG. 3A). The best threshold for electrogram duration/activation gradient in tandem (dashed line) can be used to correctly classify experiments into those with or without inducible reentry with the same accuracy as the activation gradient-uniformity threshold of FIG. 3A. In FIG. 3B the points representing experiments with short-runs of reentry (solid-triangles) tend to form a curvilinear boundary separating points representing experiments with long-runs of reentry versus no reentry.

In FIG. 4 is shown the estimated reentry isthmus (region with grid lines), the estimated wavefront direction through it (arrow), the estimated best line for ablation (dashed line), and the actual location of reentry arcs of block (thick curvy lines) for each experiment with long-runs of reentry. Panels A–Y are ordered from shortest to longest reentry cycle-length. Shown in FIG. 4W are estimates for the FIG. 1 experiment (boundary points denoted in 1D). In two experiments (O,Y), two reentry morphologies occurred and arcs of block are shown for each. For all long-runs experiments, the estimated reentry isthmus surface area mostly overlapped with actual isthmus location (mean overlap 71.3(3.2%), which was independent of heart rate (p=0.25). The XY-centers of the estimated and actual reentry isthmus were linearly correlated (X:$r^2$0.77, Y:$r^2$=0.60; p0.001). Also, the estimated best line for ablation extended across most of the width of the actual reentry isthmus (mean 88.2%).

In FIG. 5 the estimated isthmus parameters are shown for experiments with short-runs of reentry (polymorphic in A–E and monomorphic in F–K; separately ordered based on cycle-length). In three polymorphic experiments (A–C), only a single late-activating region was detected in the sinus rhythm activation map although there were isthmuses at multiple locations during reentry. In D–E, two estimated isthmuses are shown because there were two late-activating regions and therefore two primary axes during sinus rhythm. The estimates for the experiment of FIG. 2 are shown in FIG. 5F. For all short-runs experiments, the estimated reentry isthmus surface area partially overlapped actual isthmus location (mean overlap 58.6 (9.0% for monomorphic experiments, 25.7 (6.3% for polymorphic, and 43.6 (7.5% overall), which was independent of heart rate (p=0.45). The XY-centers of the estimated and actual reentry isthmuses were linearly correlated (X:$r^2$=0.78, Y:$r^2$=0.81; p<0.001). Also, the estimated best line for ablation extended across more than half the width of the actual reentry isthmus (mean 55.4%).

C) Discussion

1. Electrical Properties at the Isthmus Location

The results of this study suggest that the area over which the primary axis extends during sinus rhythm has special distinguishing electrical characteristics for experiments in which reentry was inducible versus those lacking inducibility. In experiments with monomorphic reentry, the primary axis often overlapped the actual isthmus location, which is that area of the border zone with thinnest layer of surviving myocytes [6–7] and having full-thickness gap-junctional disarray [8]. Disarray of gap-junctional intercellular connections are also present at the isthmus formation area in reentrant ventricular tachycardia in humans [10]. Uniformity of gap-junctional disarray throughout the region [8] may have been responsible for the uniform activation gradient and therefore conduction velocity uniformity (since the activating wavefront tended to propagate in parallel to the primary axis). Sinus rhythm electrogram duration tended to be short within the isthmus formation area, and longer just outside it, resulting in large differences in electrogram duration at isthmus edges that were used to draw boundary points. Electrical activation at depth is often asynchronous with surface activation [11]; therefore, reduction of electrical activity at depth, due to thinness of the layer, may have acted to shorten electrogram duration within the isthmus region.

Figure 2A:
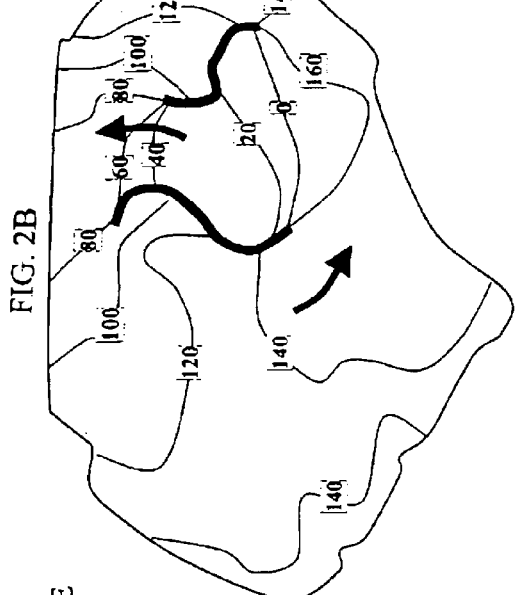
FIGS. 2A–2D are activation and electrogram duration maps for an experiment in which short-runs of monomorphic reentry were inducible by pacing from the basal margin. This figure shows that as for cases in which long-runs (greater than 10 heartbeats) are recorded, even when ventricular tachycardia is of very short duration (less than 10 heartbeats) it is possible to estimate the reentry isthmus location using sinus-rhythm activation and electrogram duration mapping. The actual reentry isthmus location is the area between the solid lines of duration map FIG. 2D for one of the cardiac cycles. For another of the cardiac-cycles, the shape changed slightly as shown by the dotted lines. The estimated reentry isthmus for this case of ventricular tachycardia is denoted by the area inscribed by the small circles, and may approximately overlap the actual reentry isthmus.
Figure 2B:
Figure 2C:
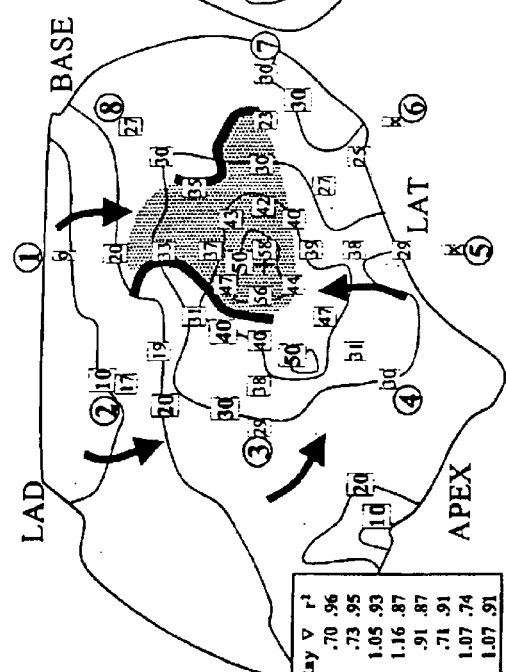
Figure 2D:
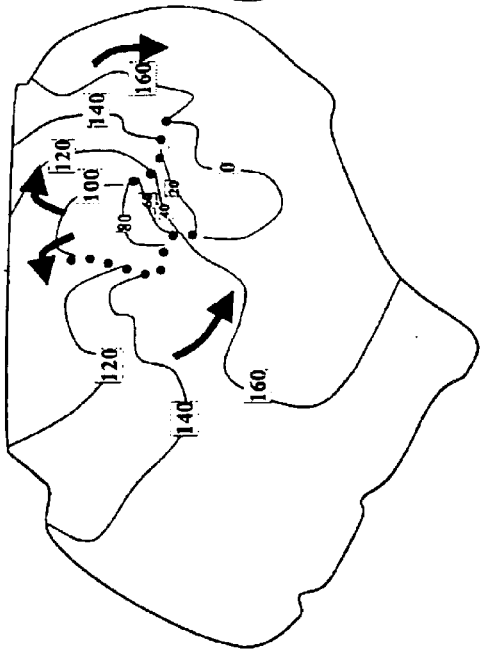

In many experiments, conduction was impeded at border areas between regions with a large disparity in electrogram duration, both during premature stimulation and during reentry (FIGS. 1B–D, 2B–D). Such border areas, or discontinuities, between regions with differing electrical properties are marked by presence of increased axial resistivity [12]. Under normal conditions, depolarizing current is sufficiently coupled across such discontinuities to maintain propagation; however, current available for activation is reduced during premature stimulation and reentry, causing slow conduction or block [12]. An arbitrary threshold of 15 ms difference in electrogram duration was used to mark areas where arcs of block would form. However, disparity in sinus rhythm electrogram duration was not always large along the entire length where block lines actually formed (FIGS. 1D, 2D). This may have resulted from diffraction effects in which wavefront curvature, as it traverses a small aperture between impassable obstacles, increases beyond a critical value so that propagation ceases [13]. Boundary points between regions with large disparity in electrogram duration would act as nearly impassable obstacles because of their high axial resistivity, whereas block would also occur along connecting segments between them, although disparity in electrogram duration is smaller, with presumably lowered axial resistivity, due to the aperture effect.

2. Clinical Significance of the Study

There is abundant evidence that ventricular tachycardia in human patients is often caused by reentrant excitation [1, 2, 5, 14]. There are several similarities between clinical observations and the measurements of electrical activation during sinus rhythm in canine hearts with and without inducible reentry. Clinical studies suggest that the extent of abnormal activation and number of fractionated electrograms tends to be greater in patients with sustained reentry compared with unsustained reentry [14], in accord with the result of this study that mean sinus rhythm electrogram duration throughout the border zone was significantly greater for experiments with long-runs of reentry versus short-runs of reentry (p<0.05). Also, clinical findings suggest that disrupted and delayed endocardial activation [14,15] and prolonged, fractionated electrograms during sinus rhythm [14] can distinguish patients with reentrant ventricular tachycardia from those with normal ventricles and those of prior infarction without reentry. In the present study, although the isthmus area tended to have short sinus rhythm electrogram duration, areas adjacent to it within the reentry circuit area often had much longer electrogram duration (FIGS. 1–2), consistent with clinical findings. Additionally, the last-activating region of the border zone during sinus rhythm tended to reside in proximity to the reentry isthmus in both clinical studies [2, 3] and in the present study. These similarities suggest that it may be possible to apply the methodology described herein to targeting of clinical ablation sites; for example using a non-contact mapping system [3]. However, differences in infarct age, the intracellular matrix, border zone location, and action potential characteristics may cause clinical data to vary significantly from canine heart data used in the present study [6], and therefore necessitate modification of the quantitative techniques.

Imprecision in activation mapping due to limited spatial resolution and/or ambiguous time of local activation at any given recording site will affect both the activation gradient measurements and localization of arcs of block. Use of a different threshold for electrogram duration measurements could alter the precise locations of boundary points. Both multiple deflections (fractionation) and a single wide deflection were considered indicative of abnormal cell presence and wavefront impediment; however, anatomic and histologic correlation to support this hypothesis was not performed in this series of experiments, which is an important limitation of this study. The results described herein for functional reentrant circuits in a canine model may not be fully applicable to reentrant ventricular tachycardia occurring in humans, where anatomical arcs of block can occur more frequently [5].

References for First Series of Experiments

1. Stevenson W G, Friedman P L, Kocovic D Z, et al. Radiofrequency catheter ablation of ventricular tachycardia after myocardial infarction. Circulation 1998;98:308–314.
2. Harada T, Stevenson W G, Kocovic D Z et al. Catheter ablation of ventricular tachycardia after myocardial infarction: relationship of endocardial sinus rhythm late potentials to the reentry circuit. JACC 1997;30:1015–1023.
3. Schilling R J, Davies D W, Peters N S. Characteristics of sinus rhythm electrograms at sites of ablation of ventricular tachycardia relative to all other sites: a non-contact mapping study of the entire left ventricle. JCE 1998;9:921–933.
4. Gardner P I, Ursell P C, Fenoglio J J Jr. et al. Electrophysiologic and anatomic basis for fractionated electrograms recorded from healed myocardial infarcts. Circulation 1985;72:596–611.
5. Ellison K E, Stevenson W G, Sweeney M O et al. Catheter ablation for hemodynamically unstable monomorphic ventricular tachycardia. JCE 2000;11:41–44.
6. Wit A L, Janse M J. Basic mechanisms of arrhythmias. In: Wit A L and Janse M J, eds. The ventricular 7. Scherlag B J, Brachman J, Kabell G et al. Sustained ventricular tachycardia: common functional properties of different anatomical substrates. In Zipes D P, Jalife J, eds. Cardiac electrophysiology and arrhythmias. Orlando Fla: Grune and Stratton; 1985:379–387.
8. Peters N S, Coromilas J, Severs N J et al. Disturbed connexin43 gap junction distribution correlates with the location of reentrant circuits in the epicardial border zone of healing canine infarcts that cause ventricular tachycardia. Circulation 1997;95:988–996.
9. Dillon S M, Allessie M A, Ursell P C et al. Influences of anisotropic tissue structure on reentrant circuits in the epicardial border zone of subacute canine infarcts. Circulation Research 1988;63:182–206.
10. Smith J H, Green C R, Peters N S et al. Altered patterns of gap junctional distribution in ischemic heart disease: an immunohistochemical study of human myocardium using laser scanning confocal microscopy. Am J Path 1991;139:801–821.
11. Miller J M, Tyson G S, Hargrove W C III et al. Arrhythmias/Pacing/Surgical correction: effect of subendocardial resection on sinus rhythm endocardial electrogram abnormalities. Circulation 1995;91:2385–2391.
12. Spach M S, Miller W T III, Dolber P C et al. The functional role of structural complexities in the propagation of depolarization in the atrium of the dog. Circulation Research 1982;50:175–191.
13. Cabo C, Pertsov A M, Baxter W T et al. Wave-front curvature as a cause of slow conduction and block in isolated cardiac muscle. Circulation Research 1994;75:1014–1028.
14. Josephson M E Zimetbaum P, Huang D. Pathophysiologic substrate for sustained ventricular tachycardia in coronary artery disease. Jap Circ J 1997;61:459–466.
15. Pogwizd S M, Corr P B. Reentrant and nonreentrant mechanisms contribute to arrhythmogenesis during early myocardial ischemia: results using three-dimensional mapping. Circulation Research 1987;61:352–371.
16. Blanchard S M, Walcott G P, Wharton J M, et al. Why is catheter ablation less successful than surgery for treating ventricular tachycardia that results from coronary artery disease? PACE 1994;17:2315–2335.
17. Ciaccio E J, Tosti A C, Scheinmann M M. Relationship between Sinus Rhythm Activation and the Reentrant Ventricular Tachycardia Isthmus. Circulation, Jul. 31, 2001.

Second Series of Experiments
A) Method
1. Clinical Recordings and Data Reduction Data was acquired using a non-contact mapping catheter (Endocardial Solutions, Inc., St. Paul, Minn.) during clinical electrophysiologic study of patients with postinfarction ventricular tachycardia who were undergoing treatment with radiofrequency catheter ablation. The non-contact catheter is positioned in the left ventricular cavity where signals are acquired and digitized, and using inverse solution mathematics, unipolar electrograms that are present across the endocardial surface are reconstructed at up to 3,360 sites [1–2]. The clinical procedure to localize the non-contact probe within the endocardial cavity and to record data, and also the physical specifications of the non-contact catheter, have been described in detail elsewhere [1–2]. This study was done retrospectively in 14 consecutive unselected patients (FIG. 13) in which ventricular tachycardia was suspected to be caused by a reentrant circuit. Approximately 20 cycles each of sinus-rhythm, ventricular pacing, ventricular tachycardia, and the pacing train leading to tachycardia onset, were extracted from the data for further analysis of 256 uniformly distributed endocardial sites (~0.5 cm spatial resolution between sites). The digital sampling rate was 1 kHz and the band pass frequency range was 0.5–500 Hz during the data acquisition and mathematical reconstruction process. The 3-dimensional locations of the 256 sites on the virtual endocardial surface (16 virtual sites along each of 16 longitudinal lines around the inside of the endocardial cavity) were translated to a 2-dimensional computerized grid using an Eckert VI projection, which is a pseudocylindrical map in which the central meridian and all parallels are at right angles, and all other meridians are sinusoidal curves. In this type of cartographic projection, some shape distortion occurs at the poles.

Activation maps of sinus-rhythm, ventricular pacing, and ventricular tachycardia were made by first marking activation times of the unipolar electrogram signals. Computer software was used to manually determine the point of sharpest slope in the signal [10], or the center point if multiple deflections with sharp slopes were present. Activation times during a selected cardiac-cycle were then printed on the 2-dimensional computerized map grid. Isochrones were set at 10–40 ms intervals, and arcs of conduction block separated sites in which activation differed by >40 ms and where wavefronts on opposite sides of the arcs moved in different directions [10]. The arcs were drawn using a cubic spline interpolation program (PSI-Plot Ver. 4, 1995 PSI) which is based on a polynomial equation that minimizes the straight-line distance to a set of boundary points. Although the actual spacing between sites was ~0.5 cm, the spline interpolation function generates a curved line that was superimposed on the computerized grid with 0.1 mm precision. The electrogram duration, defined as that contiguous series of electrogram deflections with no isoelectric segment of >5 ms duration, encompassing the time of local activation at the recording site during one cardiac cycle, was also measured for all electrogram recordings obtained during the same cycle used to construct the sinus-rhythm activation map [6]. The starting and ending points, respectively, were considered to be the beginning and ending times at which contiguous electrogram deflections arose above the isoelectric level to an amplitude >10% of the maximum electrogram peak. Electrogram duration was mapped using the same automated, 2-dimensional computerized electrode grid that was utilized for activation mapping.

2. Sinus-Rhythm Electrogram Analysis

These measurements were undertaken to determine if the isthmus of the reentrant circuit causing tachycardia could be located from analysis of electrograms obtained during sinus-rhythm. The hypothesis to be tested was that in clinical non-contact activation maps of sinus-rhythm, as in canine study activation maps [6], conduction was relatively slow and uniform where the isthmus formed. To quantify this phenomenon, the last 10 ms interval during which 5 contiguous sites activated was determined. The XY-center of this region was computed as the mean value of the site locations in the X- and Y-directions, referenced to an arbitrary fiduciary point on the computerized electrode grid [6]. A linear regression of activation times was computed along eight rays originating from the geometric center of this last-activating region (45 degree ray separation with orientation such that two of the rays were precisely vertical on the grid). The activation times at four selected sites along each ray (~0.5 cm spacing between sites), plus the center site itself (five sites in all), were used for each regression. The ray with greatest regression coefficient ($r^2 > 0.9$) and a steep activation gradient (regression line slope <0.6 m/s), if present, was termed the primary axis [6]. If none of the rays met the threshold uniformity and gradient criteria, then the XY centers of any other late-activating regions on the endocardial surface were computed and the process of searching for a primary axis meeting the above threshold criteria was repeated. If no ray originating at a late-activating region met the criteria, then the ray originating from the last-activating region with the greatest regression coefficient was taken as the primary axis. Presence of a primary axis meeting the threshold criteria was considered to indicate that an endocardial reentry circuit would be detectable in the ventricular tachycardia activation map, and its location and orientation were considered to approximate the isthmus location and wavefront propagation direction through the isthmus during reentry. Whereas, absence of a primary axis meeting the threshold criteria was considered to indicate that a complete endocardial reentry circuit would not occur during tachycardia.

For cases in which the primary axis met the threshold criteria, the isthmus shape was estimated as follows. First areas of the sinus-rhythm electrogram duration map in which the difference in electrogram duration between any two adjacent sites was 15 ms was marked on the computerized grid as described previously [6]. Selected marks around the primary axis were connected by computer algorithm so as to form the border of a contiguous region which minimized the distance between the boundary points while maintaining the surface area of the enclosed section above a minimum constraint [6]. The contiguous region so formed was termed the estimated isthmus. The percent overlap, on the computerized grid, of the surface area in which the actual isthmus determined by activation mapping was overlapped by the estimated isthmus, divided by the total surface area of the actual isthmus, was computed and tabulated. A straight line, called the estimated best ablation line, was then drawn on the computerized grid, perpendicular to the primary axis, and from one edge of the estimated isthmus to the other so as to bisect it into halves with equal areas. The percent that the estimated best ablation line spanned the actual reentry isthmus determined by activation mapping was also computed and tabulated.

3. Ventricular Tachycardia Electrogram Analysis

These measurements were undertaken to determine whether, as in canine model studies, tachycardia cycle-length is related to reentry isthmus geometry [7], and if the SCZ could be pinpointed using the electrogram acquired from any recording site in the endocardium [9]. Simple linear relationships approximated the reentry isthmus geometric shape [7–8]. The isthmus length, width, and narrowest-width were first linearized (skeletonized) from the reentry activation map computerized grids as follows (see result in FIG. 3). First the endpoint-to-endpoint distance on the computerized grid was determined for each of the two arcs of block bounding the isthmus. The average of these two lengths was taken as the skeletonized isthmus length. The distance between the endpoints of the arcs of block at the isthmus entrance and also at the isthmus exit was then determined. The average of these two distances was taken as the skeletonized isthmus width. The minimum distance between the two arcs of conduction block was termed the skeletonized narrowest-width of the isthmus.

In cases where tachycardia cycle-length changed gradually in one direction (either prolongation or shortening) by >5 ms during the ~20 beat recording interval, isthmus skeletonized parameters were computed and tabulated at the extremes in cycle length [8]. The correlation relationships of skeletonized isthmus parameters with tachycardia cycle-length, and with changes in cycle-length, were calculated and tabulated as described elsewhere [7–8]. In cases with gradual cycle-length change in one direction, a method termed piecewise-linear adaptive template matching (PLATM) was also used to approximate the timing from activation at each virtual recording site on the left ventricular endocardium to activation at the SCZ center [9]. The paradigm is based on measurement of phase shifts in the far-field deflections of the extracellular signal, which are reflective of alterations in SCZ conduction velocity [8–9]. The mean and standard error difference between the time of SCZ center activation computed with PLATM, referenced to activation at the local recording site, and the same activation interval determined by activation mapping, was calculated. All statistical computations were made using a commercial computer program (SigmaStat V2.0, Jandel Scientific).

B) Results

1. Geometry of the Reentry Circuit

Non-contact activation maps revealed that tachycardias in 11/14 patients were associated with an endocardial reentry circuit having a "figure-8" conduction pattern [5]. Examples from four cases are shown in FIGS. 8A–8D. The north and south poles of the 3-dimensional electrode distribution from the non-contact data are represented, respectively, by the top and bottom edges of the 2-dimensional grids in FIGS. 8A–8D. The left and right edges of the grids represent the place where the 3-dimensional electrode distribution was separated at a line of longitude; these edges are actually continuous with one another in 3-dimensional space. In each map, the wavefront courses through the reentry isthmus, which is bounded by arcs of conduction block (thick curvy black lines), with arrows denoting the direction of wavefront propagation. At the isthmus exit, in each case the wavefront bifurcates and travels as separate wavefronts outside the arcs of conduction block and away from the isthmus. In FIG. 8A, an arc of conduction block extends outward across the left edge of the map and continues inward from the right edge. In each panel, the separate wavefronts coalesce at the isthmus entrance. Cycle-length at onset for all tachycardias are given in FIG. 12. The mean cycle-length at onset for the 11 patients with reentrant tachycardia was 331 ms, and the mean skeletonized isthmus length, width, and narrowest-width were 5.5 cm, 4.7 cm, and 2.2 cm, respectively.

2. Isthmus Characterization from Sinus-Rhythm Electrogram Analysis

Figure 9B:
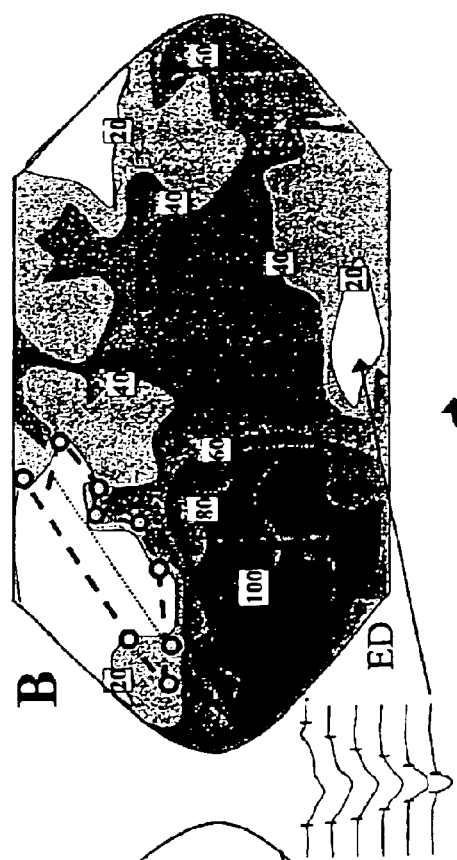
FIGS. 9A–9D show maps according to one embodiment of the present disclosure. These are an example of how sinus-rhythm electrogram analyses can be used to ascertain the position where the reentrant circuit isthmus will form in the infarct border zone, and the best line to ablate to stop ventricular tachycardia.
Figure 9A:
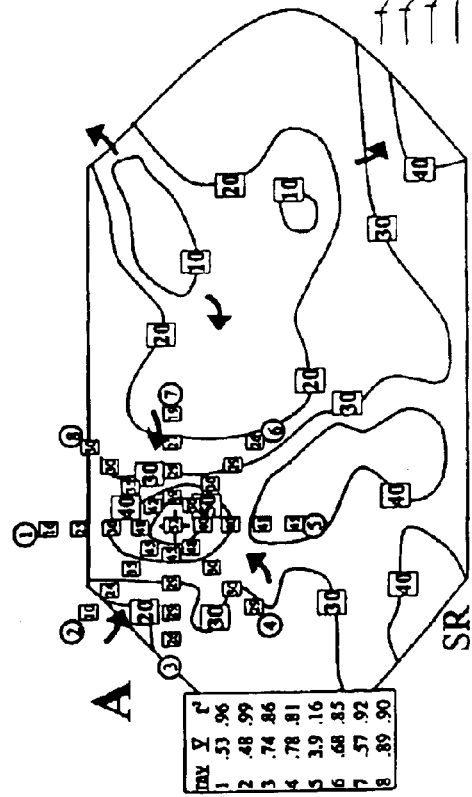
Figure 9D:
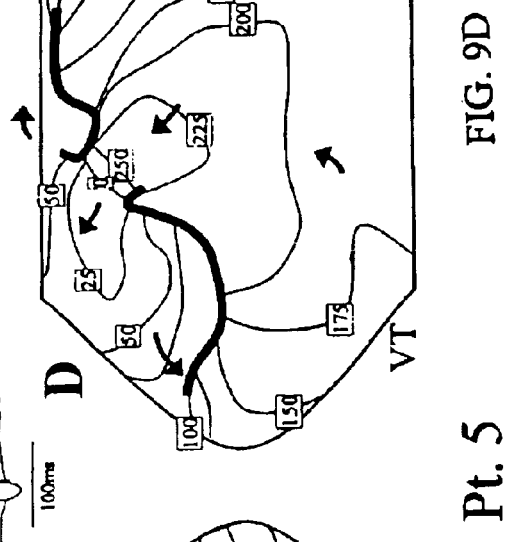
Figure 9C:
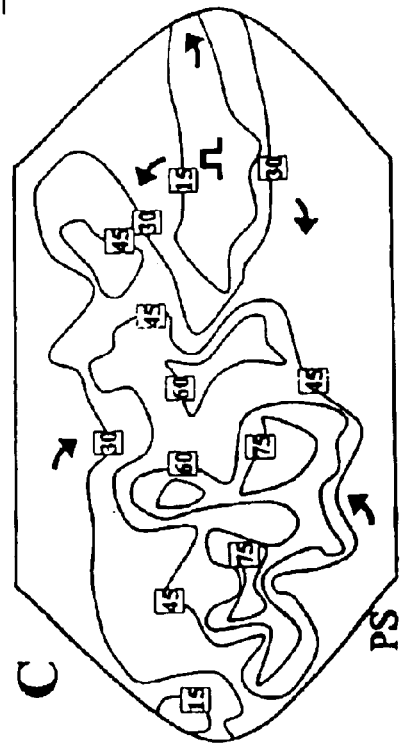

Sinus-rhythm electrogram analysis was able to localize the isthmus of the reentrant circuit. In FIGS. 9A–9B is given an example of sinus-rhythm electrogram analysis measurements (patient 5 from FIG. 12). Shown are the sinus-rhythm (FIG. 9A), premature stimulation (FIG. 9C), and reentry activation maps (FIG. 9D). During sinus-rhythm, the XY center of last-activation is denoted at the site marked "52", and the eight rays projecting from it that were used to make measurements of activation gradient and uniformity are shown in FIG. 9A, with some wrap-around to the other side of the grid). Ray 2 is the primary ray because it has greatest activation uniformity ($r^2 = 0.99$) and steepest gradient ($\nabla = 0.48$ m/s) (see table in FIG. 9A). Shown in FIG. 9B is the electrogram duration map (examples of the endpoints in duration for selected electrograms are given in the inset). The primary ray is located within a region of short electrogram duration, and the estimated isthmus and estimated best ablation line (see Methods) are denoted by the dashed polygon and dotted line, respectively, overlaid on the map grid (FIG. 9B). During premature stimulation (FIG. 9C), the large region with relatively late activation, bordered by a 60 ms isochrone, approximately coincides with an area of long sinus-rhythm electrogram duration (>60 ms, lower left in FIG. 9B). The locations of the arcs of conduction block that form during tachycardia, denoted by thick curvy lines in FIG. 9D, can be observed to partially align with boundaries between regions of greatly differing sinus-rhythm electrogram duration (FIG. 9B). The actual reentry isthmus location and shape determined by activation mapping (FIG. 9D) can be observed to approximately coincide with the reentry isthmus location and shape estimated from sinus-rhythm electrogram analysis (FIG. 9B). In each of the 11 patients in which a complete endocardial reentry circuit could be mapped (patients 1–10 and 12), a primary axis meeting the threshold criteria given in the Methods overlapped the reentry isthmus location and was in parallel with the isthmus long-axis. Whereas, a primary axis meeting the threshold criteria was absent in all 3 patients lacking a complete endocardial reentry circuit (patients 11 and 13–14).

In FIG. 10 the overlap of estimated isthmus (area enclosed by dashed line) versus the actual isthmus determined by activation mapping (gray surface bounded by superimposed arcs of block indicated by thick black lines) is shown for all 11 patients with "figure-8" reentry. The location and direction of the primary axis is given by the arrow. Frequently there is a close overlap (patients 1–2, 5–8) and the estimated best ablation line (dotted line in each panel) spans most or all of the actual isthmus width (patients 1–3, 5, 8–9, and 11). For all 11 patients, the mean overlap of the estimated isthmus with the actual isthmus was 74.2% and the estimated best ablation line spanned the actual reentry isthmus width by a mean of 83.1%.

3. Isthmus Characterization from Ventricular Tachycardia Electrogram Analysis

FIGS. 11A–11D show an example of how PLATM9 can be used to measure the time interval from local to SCZ activation (patient 9 from FIG. 12). The activation and electrogram duration map of sinus-rhythm are shown in FIGS. 11A–11B, and an activation map during pacing, and during tachycardia for short and long cardiac-cycles are shown in FIGS. 11C–11E respectively. The ray with the most uniform activity and steep gradient is ray 8 ($\nabla$=0.32, $r^2$=0.98) (FIG. 11A). Electrogram duration is short within the area where the isthmus forms (FIG. 11B). During a paced beat with a premature coupling interval, an arc of block forms (thick black line, FIG. 11C) and is coincident with a sharp transition in electrogram duration (location denoted by dashed line in FIG. 11B). Two approximately parallel arcs of conduction block (thick black lines) reside near the center of the grid during reentry (FIGS. 11D–11E). The locations of the arcs in D are also coincident with a sharp transition in electrogram duration (denoted by solid line in FIG. 11B). As in the example of FIG. 11, the isthmus has narrowed and the arcs of conduction block have shortened in length when cycle-length prolongs from FIGS. 11D to 11E. From FIGS. 11D to 11E, cycle-length prolongs from 398 to 404 ms and the wavefront decelerates at the SCZ (isochrones are more closely spaced in FIG. 11E). In the PLATM map (FIG. 11F) isochrones delineate 35 ms time intervals. PLATM times in the range (35 ms, meaning that the estimated time interval x from local to SCZ activation is −35 ms<x<35 ms, are centered near the SCZ at the narrowest span of the isthmus (FIG. 11F). The PLATM isochrones increase negatively in the direction distal to the SCZ in the circuit (meaning that SCZ activation has occurred previous to local activity) and PLATM isochrones increase positively in the direction proximal to the SCZ (meaning that SCZ activation occurs following local activity). Overall for the 5 cases in which a protracted interval of cycle-length change occurred during tachycardia, PLATM estimated the time interval from local to SCZ activation with a mean error of 19.4 ms.

C) Discussion

In this study it was determined that in the tachycardias of a select group of patients with endocardial reentry circuits, shape and length of arcs of conduction block bounding the isthmus of the figure-8 reentry circuit can change according to cycle-length, and that methods to analyze sinus-rhythm and ventricular tachycardia electrograms can be useful to discern the location and shape of circuit features without the need to construct reentry activation maps. The implication of these findings for improvement of clinical mapping procedures is now discussed.

1. The Reentry Isthmus Characterized by Sinus-Rhythm Electrogram Analysis

In all 11 patients in which a complete endocardial reentry circuit was discernable in the ventricular tachycardia activation maps, a primary axis meeting the threshold criteria given in the Methods overlapped the reentry isthmus location and was in parallel with its long-axis. (see FIGS. 9A and 11A). Presence of gap-junctional remodeling between cells extending the full thickness of the infarct border zone at the isthmus region [11] may be responsible for the reduced conduction velocity and increased uniformity of conduction that was measured along the primary axis in patients with complete endocardial reentry circuits. In the 3 patients lacking a complete endocardial reentry circuit, no primary axis meeting threshold criteria was present, suggesting that a circuit was unsustainable either because full-thickness gap-junctional remodeling was absent or because it was of insufficient surface area to support a reentrant circuit along the endocardial surface. These findings were in accord with canine model studies in which a similar methodology was used [6].

The arcs of conduction block which formed during premature stimulation and during reentry tended to overlap lines of sharp transition in sinus-rhythm electrogram duration (see FIGS. 9B and 9D, FIGS. 11B, 11C and 11D). Such boundary areas may separate regions with discontinuous electrical properties characterized by an increased effective axial resistivity [12], which would account for the slow conduction or block that was observed to occur in these regions during premature stimulation and during tachycardia. Steep transition in sinus-rhythm electrogram duration also occurred elsewhere in the infarct border zone (FIGS. 9B and 11B), and in a canine infarct model, unidirectional arcs of conduction block can also form at these regions of the border zone during premature stimulation [6]. However, it is only at the isthmus formation region, where activation during sinus-rhythm was measured to be slow and uniform, that there is most likely to be sufficient delay following premature stimulation, formation of the unidirectional arc of conduction block, and wavefront travel around the arc, so that there is recovery of excitability and genesis of reentry. Elsewhere in the infarct border zone where conduction is more rapid, the time for recovery of excitability is insufficient and reentry cannot occur.

2. The Reentry Isthmus Characterized by Ventricular Tachycardia Electrogram Analysis The findings presented herein are consistent with previous studies showing that postinfarction ventricular tachycardia in patients with coronary artery disease is often caused by a reentrant circuit with "figure-8" pattern of conduction [1–2, 4]. Although in some examples, extended arcs of conduction block were present away from the reentry isthmus (FIGS. 8A–8D), in most cases the basic pattern of activity during tachycardia was a relatively simple "figure-8" circuit. Conduction velocity was slow within the SCZ and tended to coincide with the narrowest-width of the isthmus, which may be related to a reduced current available for activation there since the isthmus is narrowed and the propagating impulse exits to a distal expansion [13–14]. In cases of gradual, protracted cycle-length change in one direction during tachycardia (prolongation or shortening), portions or all of the reentry arcs of block shifted in location; hence these segments were functional in nature. When cycle-length prolonged, the arcs of block shortened at the ends. However, the isthmus narrowest-width was a permanent fixture in the sense that arcs of block always bounded it, albeit shifts in the distance between the arcs occurred when conduction velocity changed in the SCZ. All of these findings are in accord with canine model studies in which electrogram analyses were used [6–9].

3. Relevance of Results to Clinical Catheter Ablation of Ventricular Tachycardia The results of analysis of sinus-rhythm electrograms suggests the possibility that the reentrant circuit isthmus can be located without the necessity for induction of ventricular tachycardia; however, this hypothesis requires further testing. The results of tachycardia electrogram analysis described in this study have a number of implications for ablation of tachycardia. That the ends of the arcs were not permanent fixtures during periods of reentry cycle-length change offers a possible explanation as to why radiofrequency catheter ablation may stop tachycardia that is induced during clinical electrophysiologic study, but tachycardia is sometimes reinducible thereafter [4]. If wavefront deceleration occurs in the SCZ and there is no other change in conduction velocity around the circuit, the spatial excitable gap [15] will increase outside the SCZ. Hence, there will be increased time for recovery of excitability away from the SCZ, which will mostly affect the ends of the functional arcs of conduction block, because the cells there are closest to having recovered excitability [5]. Therefore, if an ablation lesion is created near the ends of the arcs of conduction block and cycle-length is volatile, it may prevent successful passage of the electrical impulse through the diastolic region at certain (shorter) cycle-lengths when the arcs are relatively long (FIG. 11D), because there is less time for recovery of excitability. However at other (longer) cycle-lengths when the arcs are shorter in length (FIG. 11E), the lesion would then be exterior to the isthmus so that the impulse could successfully bypass it, causing reentry to persist.

Furthermore, even when ablating toward the center of the diastolic region, since isthmus width can vary with cycle-length when arcs of conduction block are functional, an ablation lesion that scarcely spans the isthmus at longer cycle-lengths when it is narrow may not span it at shorter cycle-lengths when it is wider, thereby allowing the impulse to propagate around the lesion and tachycardia to persist. Indeed, it has been reported that the ablation lesion sometimes acts to prolong tachycardia cycle-length but not stop tachycardia, as would be expected if the wavefront were impeded but not blocked by an ablation lesion that did not fully span the isthmus width over all possible tachycardia cycle-lengths [16]. At present it is unknown how tachycardia cycle-length, functional arcs of conduction block, and ablation lesion location dynamically interact, a subject of future research. However, to ensure that the lesion entirely spans the isthmus for the duration of tachycardia even when the circuit is changing dynamically, it may be prudent to ablate across the isthmus at its narrowest-width, which is likely to be a permanent fixture during tachycardia, and for the ablation lesion to transect the isthmus to greater than its actual span during the mapped cycle, since width may increase should cycle-length shorten. Although changes in wavefront speed within the SCZ may not always occur naturally during tachycardia, administration of drugs preferential to the area [17] may specifically alter SCZ activation so that the region can still be localized using electrogram analyses.

4. Future Directions

The translation of the 3-dimensional virtual electrode array location onto the 2-dimensional grid causes some distortion in the shape of the reentry isthmus and the pattern of activation. The mathematical reconstruction process is most accurate at the equatorial regions of the non-contact catheter; circuits with components near the polar regions are likely to be less accurately represented in the activation maps [1–2]. However, the electrogram analyses described herein were relative measurements and hence by reverse distortion, parameters are correctable to the original 3-dimensional space. A relatively low spatial resolution of recording electrodes was used in the study (~0.5 cm spacing). Higher spatial resolution can be obtained using the non-contact catheter [1–2]; however, analysis complexity would increase. The signal strength from the endocardial surface is much greater during systole than diastole [1–2]; thus diastolic components of the reconstructed electrograms are of low amplitude and diastolic activation times are more difficult to discern, introducing some degree of error into the measurements. In the present study, the estimated isthmus location and shape were not compared with the locations of sites in which concealed entrainment occurred during pace mapping [4], nor with the locations of sites in which ablation caused termination of tachycardia without recurrence; however, a confirmatory study of this type is planned for the future. Such information might also be useful to determine whether electrogram analyses can predict where to best ablate to stop tachycardia when a complete endocardial reentry circuit is absent. Although the notion of an estimated best ablation line was introduced during this retrospective analysis, testing of such must be reserved for a future, prospective study.

References for Second Series of Experiments

1. Schilling R J, Peters N S, Davies D W. Simultaneous endocardial mapping in the human left ventricle using a non-contact catheter. Circulation 1998;98:887–898.
2. Schilling R J, Peters N S, Davies D W. Feasibility of a non-contact catheter for endocardial mapping of human ventricular tachycardia. Circulation 1999;99:2543–2552.
3. Blanchard S M, Walcott G P, Wharton J M, et al. Why is catheter ablation less successful than surgery for treating ventricular tachycardia that results from coronary artery disease? PACE 1994;17:2315–2335.
4. Stevenson W G, Friedman P L, Kocovic D, et al. Radiofrequency catheter ablation of ventricular tachycardia after myocardial infarction. Circulation 1998;98:308–314.
5. El-Sherif N. The figure-8 model of reentrant excitation in the canine postinfarction heart. In Zipes DP, Jalife J, eds: Cardiac Electrophysiology: From Cell to Bedside. W B Saunders, Philadelphia, 1995, pp 363–378.

6. Ciaccio E J, Tosti A C, Scheinman M M. Relationship between sinus-rhythm activation and the reentrant ventricular tachycardia isthmus. Circulation 2001 (in press).
7. Ciaccio E J, Costeas C A, Coromilas J, et al. Static relationship of cycle-length to reentrant circuit geometry. Circulation 2001 (submitted).
8. Ciaccio E J. Dynamic relationship of cycle length to reentrant circuit geometry and to the slow conduction zone during ventricular tachycardia. Circulation 2001;103:1017–1024.
9. Ciaccio E J. Localization of the slow conduction zone during reentrant ventricular tachycardia. Circulation 2000;102: 464–469.
10. Dillon S M, Allessie M A, Ursell P C, et al. Influences of anisotropic tissue structure on reentrant circuits in the epicardial border zone of subacute canine infarcts. Circulation Research 1988;63:182–206.
11. Peters N S, Coromilas J, Severs N J, et al. Disturbed connexin43 gap-junction distribution correlates with the location of reentrant circuits in the epicardial border zone of healing canine infarcts that cause ventricular tachycardia. Circulation 1997;95:988–996.
12. Spach M S, Miller W T III, Dolber P C, et al. The functional role of structural complexities in the propagation of depolarization in the atrium of the dog. Circulation Research 1982;50:175–191.
13. Kogan B Y, Karplus W J, Billett B S, et al: Excitation wave propagation within narrow pathways: Geometric configurations facilitating unidirectional block and reentry. Physica D 1992;59:275–296.
14. Rohr S, Salzberg B M. Characterization of impulse propagation at the microscopic level across geometrically defined expansions of excitable tissue: multiple site optical recording transmembrane voltage (MSORTV) in patterned growth heart cell cultures. J Gen Physiol 1994;104:287–309.
15. Peters N S, Coromilas J, Hanna M S, et al. Characteristics of the temporal and spatial excitable gap in anisotropic reentrant circuits causing sustained ventricular tachycardia. Circ Res 1998;82:279–293.
16. Sato M, Sakurai M, Yotsukura A, et al. The efficacy of radiofrequency catheter ablation for the treatment of ventricular tachycardia associated with cardiomyopathy. Jpn Circ J. 1997;61:55–63.
17. Chinushi M, Aizawa Y, Miyajima S, et al. Proarrhythmic effects of antiarrhythmic drugs assessed by electrophysiologic study in recurrent sustained ventricular tachycardia. Jpn Circ J 1991;55:133–141.

What is claimed is:

1. A method for identifying and localizing a reentrant circuit isthmus in a heart of a subject during sinus rhythm, comprising the steps of:
  a) receiving electrogram signals from the heart during sinus rhythm via electrodes;
  b) creating a map based on the received electrogram signals;
  c) determining, based on the map, a location of the reentrant circuit isthmus in the heart; and
  d) displaying the location of the reentrant circuit isthmus.

2. The method of claim 1, wherein step b) includes arranging activation times of the received electrogram signals based on a position of the respective electrodes.

3. The method of claim 2, wherein the activation times are measured from a predetermined start time until reception of a predetermined electrogram signal.

4. The method of claim 2, wherein the map includes isochrones for identifying electrogram signals having activation times within a predetermined range.

5. The method of claim 2, wherein step c) includes finding a center reference activation location on the map by averaging an electrode coordinate position of a predetermined number of electrogram signals selected based on an activation time.

6. The method of claim 5, wherein step c) includes defining measurement vectors originating from the center reference activation location and extending outward on the map, the measurement vectors used to designate the electrodes located along the measurement vectors.

7. The method of claim 6, wherein the electrodes assigned to a measurement vector are chosen according to a distance from the measurement vector.

8. The method of claim 6, wherein the electrodes assigned to a measurement vector are a subset of the electrodes chosen according to a distance from the measurement vector.

9. The method of claim 6, wherein step c) includes selecting from the measurement vectors a primary axis vector having one of an activation gradient value within a predetermined range and a highest activation uniformity value within a predetermined range and where the primary axis vector indicates a location of the reentrant circuit isthmus.

10. The method of claim 9, wherein the activation uniformity value is a coefficient of linear regression.

11. The method of claim 9, wherein the activation uniformity value is a coefficient of non-linear regression.

12. The method of claim 9, wherein the activation uniformity value is a variance in activation times along a selected measurement vector.

13. The method of claim 9, wherein the activation uniformity value is a measure of variability along a selected measurement vector.

14. The method of claim 9, wherein the activation gradient value is a slope of a linear regression line.

15. The method of claim 9, wherein the activation gradient value is a slope of a non-linear regression line.

16. The method of claim 9, wherein the activation gradient value is a mean absolute difference in activation times along a selected measurement vector.

17. The method of claim 9, wherein the activation gradient value is a difference along the measurement vector.

18. The method of claim 9, wherein step c) includes, when a primary axis vector is not found,
  i) finding an alternate center reference activation location on the map by averaging an electrode coordinate position of a predetermined number of electrogram signals having an alternate characteristic,
  ii) defining measurement vectors originating from the alternate center reference activation location and extending outward on the map, the measurement vectors used to designate the electrodes located along the vectors, and
  iii) selecting from the measurement vectors a primary axis vector having one of an activation gradient value within a predetermined range and a highest activation uniformity value within a predetermined range.

19. The method of claim 18, wherein step d) includes when a primary axis vector is not found, selecting from the measurement vectors a primary axis vector having one of an activation uniformity value within a predetermined range and a highest gradient value within a predetermined range.

20. The method of claim 9, further comprising the step of:
  e) determining, based on the map, a shape of the reentrant circuit isthmus in the heart; and f) displaying the shape of the reentrant circuit isthmus.

21. The method of claim 20, wherein step b) includes generating duration values representing a time difference between a starting point and a stopping point in the electrogram signals.

22. The method of claim 21, wherein the one of the starting point and stopping point is computed to be when an amplitude of the electrogram signal is within a predetermined amount of an amplitude of the electrogram signal.

23. The method of claim 21, wherein step e) includes finding threshold points in which the difference in electrogram duration values between adjacent sites is greater than a predetermined time interval.

24. The method of claim 23, wherein step e) includes connecting the threshold points to form a polygon encompassing the center reference activation location.

25. The method of claim 24, wherein step e) includes connecting the threshold points to form a polygon encompassing the center reference activation location and a predetermined portion of the primary axis vector and indicating a shape of the reentrant circuit isthmus in the heart.

26. The method of claim 25, further comprising the step of:
   g) determining an ablation line to ablate the heart based on the location of the reentrant circuit isthmus; and
   h) displaying the ablation line.

27. The method of claim 26, wherein step g) includes drawing the ablation line on the map bisecting the polygon and at a predetermined angle with respect to the primary axis vector.

28. The method of claim 27, wherein the ablation line traverses the polygon plus a predetermined distance.

29. A method for identifying and localizing a reentrant circuit isthmus in a heart of a subject during sinus rhythm, comprising the steps of:
   a) receiving electrogram signals from the heart during sinus rhythm via electrodes;
   b) creating a map based on the received electrogram signals;
   c) finding a center reference activation location on the map;
   d) defining measurement vectors originating from the center reference activation location;
   e) selecting from the measurement vectors a primary vector indicating a location of the reentrant circuit isthmus in the heart; and
   f) displaying the location of the reentrant circuit isthmus.

30. The method of claim 29, further comprising the steps of:
   g) finding threshold points of the electrogram signals on the map;
   h) connecting the threshold points to form a polygon indicating a shape of the reentrant circuit isthmus in the heart; and
   i) displaying the shape of the reentrant circuit isthmus.

31. The method of claim 28, further comprising the step of:
   j) finding an ablation line based on the polygon; and
   k) displaying the ablation line.

32. A system for identifying and localizing a reentrant circuit isthmus in a heart of a subject during sinus rhythm, comprising:
   a) an interface for receiving electrogram signals from the heart during sinus rhythm via electrodes;
   b) processing means for creating a map based on the received electrogram signals, and determining, based on the map, a location of the reentrant circuit isthmus in the heart; and
   c) a display adapted to display the location of the reentrant circuit isthmus.

33. A system for identifying and localizing a reentrant circuit isthmus in a heart of a subject during sinus rhythm, comprising:
   a) receiving means for receiving electrogram signals from the heart during sinus rhythm via electrodes;
   b) storage means for storing electrogram data corresponding to the electrogram signals received by the receiving means;
   c) processing means for retrieving the electrogram data, creating a map based on the electrogram signals, finding a center reference activation location on the map, defining measurement vectors originating from the center reference activation location, selecting from the measurement vectors a primary axis vector indicating a location of the reentrant circuit isthmus in the heart, finding threshold points of the electrogram signals on the map, and connecting the threshold points to form a polygon indicating a shape of the reentrant circuit isthmus in the heart; and
   d) a display for displaying one of the location and shape of the reentrant circuit isthmus.

* * * * *